(12) United States Patent
Tazi et al.

(10) Patent No.: US 9,061,999 B2
(45) Date of Patent: Jun. 23, 2015

(54) COMPOUNDS USEFUL FOR TREATING AIDS

(75) Inventors: Jamal Tazi, Clapiers (FR); Florence Mahuteau, Saint Remy les Chevreuses (FR); Romain Najman, L'Hay-les-Roses (FR); Didier Scherrer, Castelnau le Lez (FR); Noëlie Campos, Le Cres (FR); Aude Garcel, Le Cres (FR)

(73) Assignees: ABIVAX, Paris (FR); CENTRE NATIONAL DE LA RECHERCHE SCIENTIFIQUE, Paris (FR); INSTITUT CURIE, Paris (FR); UNIVERSITE MONTPELLIER 2, Montpellier (FR)

( * ) Notice: Subject to any disclaimer, the term of this patent is extended or adjusted under 35 U.S.C. 154(b) by 0 days.

(21) Appl. No.: 13/993,990

(22) PCT Filed: Dec. 13, 2011

(86) PCT No.: PCT/IB2011/055643
§ 371 (c)(1),
(2), (4) Date: Jun. 13, 2013

(87) PCT Pub. No.: WO2012/080953
PCT Pub. Date: Jun. 21, 2013

(65) Prior Publication Data
US 2013/0267703 A1  Oct. 10, 2013

(30) Foreign Application Priority Data
Dec. 15, 2010 (EP) ..................... 10306417

(51) Int. Cl.
*A61K 31/04* (2006.01)
*C07D 215/38* (2006.01)
(Continued)

(52) U.S. Cl.
CPC ............ *C07D 215/38* (2013.01); *C07D 401/12* (2013.01); *C07D 295/135* (2013.01)

(58) Field of Classification Search
CPC .. A01B 12/006; C07D 215/38; C07D 401/12; C07D 295/135
USPC ........................................................ 546/159
See application file for complete search history.

(56) References Cited

U.S. PATENT DOCUMENTS 7,019,147 B1 * 3/2006 Barth et al. .................... 548/125
2004/0038969 A1 2/2004 Doherty et al.

(Continued)

FOREIGN PATENT DOCUMENTS

EP 0 394 112 A2 10/1990
FR 2 387 229 A1 11/1978
(Continued)

OTHER PUBLICATIONS

Brandt, Biochimica et Blophysica Acta, Protein Sturcutre and Molecular Enzymology, vol. 1101(1), pp. 41-47, 1992, abstract only CA 117:82915.*
Jun. 27, 2011 International Search Report issued in International Patent Application No. PCT/IB2010/052652.
Jun. 27, 2011 Written Opinion of the International Searching Authority issued in International Patent Application No. PCT/IB2010/052652.
Aug. 9, 2011 International Search Report issued in International Patent Application No. PCT/IB2010/052651.
(Continued)

*Primary Examiner* — D M Seaman
(74) *Attorney, Agent, or Firm* — Oliff PLC

(57) ABSTRACT

The present invention relates to compound (I)

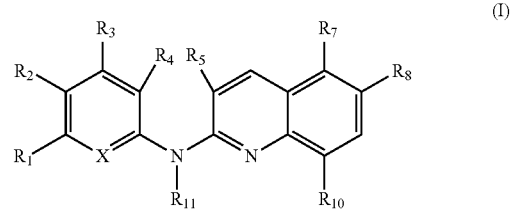

(I)

for use as an agent for preventing, inhibiting or treating AIDS, wherein X is $CR_0$ or N; $R_0$, $R_1$, $R_2$, $R_3$, $R_4$, $R_7$ and $R_8$ independently represent a hydrogen atom, a halogen atom or a group chosen among a ($C_1$-$C_5$)alkyl group, a ($C_3$-$C_6$)cycloalkyl group, a ($C_1$-$C_5$)fluoroalkyl group, a ($C_1$-$C_5$)alkoxy group, a ($C_1$-$C_5$)fluoroalkoxy group, a —CN group, a —$COOR_a$ group, a —$NO_2$ group, a —$NR_aR_b$ group, a —$NR_a$—$SO_2$—$NR_aR_b$ group, a —$NR_a$—$SO_2$—$R_a$ group, a —$NR_a$—C(=O)—$R_a$ group, a —$NR_a$—C(=O)—$NR_aR_b$ group, a —$SO_2$—$NR_aR_b$ group, a —$SO_3H$ group, a —OH group, a —O—$SO_2$—$OR_c$ group, a —O—P(=O)—($OR_c$)($OR_d$) group, a —O—$CH_2$—$COOR_c$ group and can further be a group chosen among:

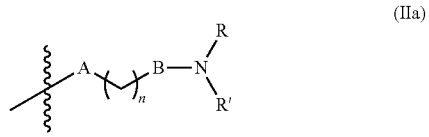

(IIa)

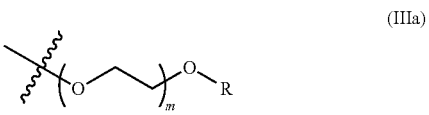

(IIIa)

$R_5$ represents a hydrogen atom, a ($C_1$-$C_5$)alkyl group or a ($C_3$-$C_6$)cycloalkyl group; $R_{10}$ is a hydrogen atom or a chlorine atom, and $R_{11}$ is a hydrogen atom or a ($C_1$-$C_4$)alkyl group or anyone of its pharmaceutically acceptable salts.

14 Claims, No Drawings

(51) Int. Cl.
C07D 401/12 (2006.01)
C07D 295/135 (2006.01)

(56) References Cited

U.S. PATENT DOCUMENTS

| | | |
|---|---|---|
| 2005/0119225 A1 | 6/2005 | Schumacher et al. |
| 2006/0089380 A1 | 4/2006 | Barnham et al. |
| 2008/0161353 A1 | 7/2008 | Barnham et al. |
| 2011/0003843 A1 | 1/2011 | Lejeune et al. |

FOREIGN PATENT DOCUMENTS

| | | |
|---|---|---|
| FR | 2 436 786 A1 | 4/1980 |
| FR | 2 627 493 A1 | 8/1989 |
| FR | 2 645 861 A1 | 10/1990 |
| FR | 2 849 474 A1 | 3/2005 |
| FR | 2 859 475 A1 | 3/2005 |
| WO | WO 00/59875 | 10/2000 |
| WO | WO 2004/007461 A1 | 1/2004 |
| WO | WO 2004/078731 A1 | 9/2004 |
| WO | WO 2005/023255 A2 | 3/2005 |
| WO | WO 2006/081444 A2 | 8/2006 |
| WO | WO 2008/003864 A1 | 1/2008 |
| WO | WO 2008/008234 A1 | 1/2008 |
| WO | WO 2008/101935 A2 | 8/2008 |
| WO | WO 2008/115870 A2 | 9/2008 |
| WO | WO 2008/143440 A1 | 11/2008 |
| WO | WO 2009/023844 A2 | 2/2009 |
| WO | WO 2009/087238 A2 | 7/2009 |
| WO | WO 2010/143168 A2 | 12/2010 |
| WO | WO 2010/143169 A2 | 12/2010 |

OTHER PUBLICATIONS

Aug. 9, 2011 Written Opinion of the International Searching Authority issued in International Patent Application No. PCT/IB2010/052651.
Apr. 13, 2011 International Search Report issued in International Patent Application No. PCT/IB2010/052650.
Apr. 13, 2011 Written Opinion of the International Searching Authority issued in International Patent Application No. PCT/IB2010/052650.
Dec. 10, 2009 Partial European Search Report issued in European Patent Application No. 09162630.9.
Nov. 19, 2009 European Search Report issued in European Patent Application No. 09305540.
Vulliamy et al., "Mutations in the Telomerase Component NHP2 Cause the Premature Ageing Syndrome Dyskeratosis Congenita," PNAS, 2008, vol. 105, No. 23, pp. 8073-8078.
Brune et al., "Progeria: A New Kind of Laminopathy—Clinical and Molecular Update of the Hutchinson-Gilford Syndrome," 1$^{st}$ European Symposium, 2003.
Park et al., "Efficient Palladium-Catalyzed Amination of Aryl Chlorides Using Dicyclo-hexylamino[(2,6-dimethyl)morpholino]phenylphosphine as a PN$_2$ Ligand," Synthesis, 2009, No. 5, pp. 0815-0823.
Loones et al., "Examination of the Mechanism of the Intramolecular Amination of N-(3-bromopyridin-2-yl)azaheteroarylamines and N-(2-chloropyridin-3-yl)azaheteroarylamines: a Pd-catalyzed Amination and/or a Base-Assisted Nucleophilic Aromatic Substitution?," Tetrahedron, 2007, vol. 63, pp. 3818-3825.
Dhanabal et al., "Heteroatom Directed Photoannulation: Synthesis of Indoloquinoline Alkaloids: Cryptolepine, Cryptotackieine, Cryptosanguinolentine, and their Methyl Derivatives," Tetrahedron, 2006, vol. 62, pp. 6258-6263.
Boganyi et al.,"Syntheses of New Quinoline-Containing Heterocyclic Scaffolds Using Inter- and Intramolecular Pd-Catalyzed Amination," Journal of Heterocyclic Chemistry, 2009, vol. 46, No. 1, pp. 33-38.
Fors et al., "An Efficient Process for Pd-Catalyzed C-N Cross-Coupling Reactions of Aryl Iodides: Insight Into Controlling Factors," Journal of the American Chemical Society, 2009, vol. 131, No. 16, 5766-5768.
Jonckers et al., "Selective Palladium-Catalyzed Aminations of Dicholoropyridines," Tetrahedron, 2001, vol. 57, pp. 7027-7034.
Kaczmarek et al., "Synthesis and Antineoplastic Properties of Some Benzoiso-.Alpha.-Carbolines," Archiv Der Pharmazie, Weinheim, Germany, 1988, vol. 321, No. 8, pp. 463-467.
Loones et al., "Synthesis of Pyrido[2', 1':2,3]imidazo[4,5-b]quinoline and pyrido[1',2':1,2]imidazo [4,5b]quinoline and their Benzo and Aza Analogs via Tandem Catalysis," Tetrahedron, 2007, vol. 63, pp. 8954-8961.
Solekhova et al., "Reductive Amination of Quinoline N-Oxide with Aminopyridines and their N-Tosyl Derivatives," Russian Journal of Organic Chemistry, 2002, vol. 38, No. 8, pp. 1192-1194.
Nguyen et al., "Synthesis and Biological Evaluation of Amino-Substituted Benzo [f]pyrido[4,3-b] and Pyrido [3,4-b]quinoxalines: a New Class of Antineoplastic Agents," Anti-Cancer Drug Design, 1995, vol. 10, No. 4, 277-97 (abstract only).
Baklanov et al., "Photocyclization of (o-haloaryl)hetarylamines," Zhurnal Organicheskoi Khimii, 1991, vol. 27, No. 3, pp. 638-649 (abstract only).
Ducrocq et al., "Synthesis of 10-substituted 5H-pyrido[3', 4':4,5]pyrrolo[2,3-]isoquinolines," Journal of the Chemical Society, Perkin Transactions 1: Organic and Bio-Organic Chemistry (1972-1999), 1979, vol. 1, pp. 142-145.
Prostakov et al., "Schiff Bases in Syntheses of Substituted Naphthylamines, Napthyridines, Azophenanthrenes, and Benzocarbazole," Khimiya Geterotsiklicheskikh Soedinenii, 1972, vol. 10, pp. 1400-1403 (abstract only).
Grout et al., "Polyazabenzo[a]pyrenes," Journal of the Chemical Society [Section] C: Organic, 1968, vol. 21, pp. 2689-2693.
Talik et al., "2-Chloro-3, 5-dinitropyridine. I. Exchange Reactions of the Chlorine Atom," Bulletin de L'Academie Polonaise des Sciences, Serie Des Sciences Chimiques, 1960, vol. 8, No. 5, pp. 219-222 (abstract only).
Deuerleine, "Dipryridyl-, diquinolyl-, and Pyridylquinolylamines," Journal fuer Praktische Chemie (Liepzig), 1923, vol. 106, pp. 53-65 (abstract only).
Kondratenko et al., "Bactericidal Activity of Some Derivatives of N-heteroaromatic Compounds," Mikrobiologichnii Zhurnal, 1934-1977, 1978, vol. 40, No. 3, pp. 368-370 (abstract only).
Gritsenko et al., "Synthesis in Phenothiazines. XXXIX. Dimethylpyridophenothiazines," Khimiya Geterotsiklicheskikh Soedinenii,1975, vol. 1, pp. 50-54 (abstract only).
Buchmann et al., "The Preparation and Reactivity of 4-hydroxy-7-chloroquinaldine," Journal fuer Praktische Chemie, 1962, vol. 17, pp. 135-146 (abstract only).
Khalifa, "Hutchinson-Gilford Progeria Syndrome: Report of a Libyan Family and Evidence of Autosomal Recessive Inheritance," Clinical Genetics, 1989, vol. 35, pp. 125-132.
De Sandre-Giovannoli et al., "Lamin A Truncation in Hutchinson-Gilford Progeria," Science, 2003, vol. 300, p. 2055.
Pendas et al., "Defective Prelamin A Processing and Muscular and Adipocyte Alterations in Zmpste24 Metalloproteinsase-deficient Mice," Nature Genetics, 2002, vol. 31, pp. 94-99.
De Sandre-Giovannoli et al., "Altered Splicing in Prelamin A-associated Premature Aging Phenotypes," Progress in Molecular and Subcellular Biology, 2006, pp. 199-232.
Fong et al., "A Protein Farnesyltransferase Inhibitor Ameliorates Disease in a Mouse Model of Progeria," Science, 2006, vol. 311, pp. 1621-1623.
Varela et al., "Combined Treatment with Statins and Aminobisphosphonates Extends Longevity in a Mouse Model of Human Premature Aging," Nature Medicine, 2008, vol. 14, No. 7, pp. 767-772.
Labourier et al., "Recognition of Exonic Splicing Enhancer Sequences by the *Drosophila* Splicing Repressor RSF1," Nucleic Acids Research, 1999, vol. 27, No. 11, pp. 2377-2386.
Dignam et al., "Eukaryotic Gene Transcription with Purified Components," Methods in Enzymology, 1983, vol. 101, pp. 582-598.
Tazi et al., "A Protein that Specifically Recognizes the 3' Splice Site of Mammalian Pre-mRNA Introns is Associated with a Small Nuclear Ribonucleoprotein," Cell, 1986, vol. 47, pp. 755-766.
Sanchez-Martin et al., "Symmetrical Bis-Quinolinium Compounds: New Human Choline Kinase Inhibitors with Antiproliferative Activ-

(56) References Cited

OTHER PUBLICATIONS ity against the HT-29 Cell Line," Journal of Medicinal Chemistry, 2005, vol. 48, No. 9 pp. 3354-3363.
Cottet et al., "Recommendable Routes to Trifluoromethyl-Substituted Pyridine-and Quinolinecarboxylic Acids," Eur. J. Org. Chem., 2003, pp. 1559-1568.
Balkau et al., "Synthesis of Ellipticine Intermediates: 6-Amino-, 6-hydroxy-, and 6-Methoxy-5,8-Dimethylisoquinoline," Australian. J. Chem., 1969, vol. 22, pp. 2489-2492.
Sharp, "Split Genes and RNA Splicing," Cell, 1994, vol. 77, pp. 805-815.
Black, "Mechanisms of Alternative Pre-Messenger RNA Splicing," Annu. Rev. Biochem., 2003, vol. 72, pp. 291-336.
Manley et al., "SR Proteins and Splicing Control," Genes & Development,1996, vol. 10, pp. 1569-1579.
Graveley, "Sorting out the Complexity of SR Protein Functions," RNA, 2000, vol. 6, pp. 1197-1211.
Wang et al., "SC35 Plays a Role in T Cell Development and Alternative Splicing of CD45," Molecular Cell, 2001, vol. 7, pp. 331-342.
Ewing et al., "Analysis of Expressed Sequence Tags Indicates 35,000 Human Genes," Nature Genetics, 2000, vol. 25, pp. 232-234.
Johnson et al., "Genome-Wide Survey of Human Alternative Pre-mRNA Splicing with Exon Junction Microarrays," Science, vol. 302, pp. 2141-2144, 2003.
Cartegni et al., "Listening to Silence and Understanding Nonsense: Exonic Mutations that Affect Splicing," Nature Reviews—Genetics, Apr. 2002, vol. 3, pp. 285-298.
Tazi et al., "The Spliceosome: a Novel Multi-faceted Target for Therapy," Trends in Biochemical Sciences, 2005, vol. 30, No. 8, pp. 469-478.
Nissim-Rafinia et al., "Cellular and Viral Splicing Factors Can Modify the Splicing Pattern of CFTR Transcripts Carrying Splicing Mutations," Human Molecular Genetics, 2000, vol. 9, No. 12, pp. 1771-1778.
Hofmann et al., "Htra2-β1 Stimulates an Exonic Splicing Enhancer and can Restore Full-length SMN Expression to Survival Motor Neuron 2 (SMN2)," PNAS, 2000, vol. 97, No. 17, pp. 9618-9623.
Sazani et al., "Systemically Delivered Antisense Oligomers Upregulate Gene Expression in Mouse Tissues," Nature Biotechnology, 2002, vol. 20, pp. 1228-1233.
Sazani et al., "Modulation of Alternative Splicing by Antisense Oligonucleotides," Prog. Mol. Subcell. Biol., vol. 31, pp. 217-239, 2003.
Cartegini et al., "Correction of Disease-associated Exon Skipping by Synthetic Exon-specific Activators," Nature Structural Biology, 2003, vol. 10, No. 2, pp. 120-125.
Andreassi et al., "Aclarubicin Treatment Restores SMN Levels to Cells Derived from Type 1 Spinal Muscular Atrophy Patients," Human Molecular Genetics, 2001, vol. 10, No. 24, pp. 2841-2849.
Liu et al., "Partial Correction of Endogenous F508 CFTR in Human Cystic Fibrosis Airway Epithelia by Spliceosome-mediated RNA Trans-splicing," Nature Biotechnology, 2002, vol. 20, pp. 47-52.
Bakkour et al., "Small-Molecule Inhibition of HIV pre-mRNA Splicing as a Novel Antiretroviral Therapy to Overcome Drug Resistance," PLOS Pathogens, 2007, vol. 3, issue 10, pp. 1530-1539.
Connor et al., "Vpr is Required for Efficient Replication of Human Immunodeficiency Virus type-1 in Mononuclear Phagocytes," Virology, (1995), vol. 206, pp. 935-944.
Wang et al., "Alternative isoform regulation in human tissue transcriptomes, "Nature, vol. 456, pp. 470-476, Nov. 2008.
Pan et al., "Deep surveying of alternative splicing complexity in the human transcriptome by high-throughput sequencing, "Nature Genetics, vol. 40, No. 12, pp. 1413-1415, Dec. 2008.

F. J. Leinweber, "Possible Physiological Roles of Carboxylic Ester Hydrolases," Drug Metabolism Reviews, vol. 18, No. 4, pp. 379-439, 1987.
Mar. 9, 2012 International Search Report issued in International Patent Application No. PCT/IB2011/055643.
Jun. 18, 2013 International Preliminary Report on Patentability issued in International Patent Application No. PCT/IB2011/055643.
U.S. Appl. No. 13/377,745 in the name of Roux et al., filed Jul. 5, 2012.
U.S. Appl. No. 13/377,753 in the name of Tazi et al., filed Jun. 4, 2012.
U.S. Appl. No. 13/377,760 in the name of Tazi et al., filed Jul. 2, 2012.
U.S. Appl. No. 13/993,990 in the name of Tazi et al., filed Jul. 13, 2012.
Loriga et al., "Quinoxaline chemistry. Part 8. 2-[Anilino1-3-[carboxyl-6(7)-substituted quinoxalines as non classical antifolate agents. Synthesis and evaluation of in vitro anticancer, anti-HIV and antifungal activity," Farmaco 5:531-37 (1997).
Loriga et al., "Quinoxaline chemistry. Part 7. 2-[aminobenzoatesl-and 2-[aminobenzoylglutamate]-quinoxalines as classical antifolate agents. Synthesis and evaluation of in vitro anticancer, anti-HIV and antifungal activity," Farmaco 52:157-66 (PubMed Abstract No. 9212450) (1997).
Nov. 21, 2013 Office Action issued in U.S. Appl. No. 13/377,760.
Dec. 23, 2013 Office Action issued in U.S. Appl. No. 13/377,753.
El-Sayed et al., "Synthesis of Some Novel Quinoline-3-carboxylic Acids and Pyrimidoquinoline Derivatives as Potential Antimicrobial Agents", Archiv der Pharmize, 2002, pp. 403-410, vol. 335(9).
Silberg et al., "N-Acyl-N, N-dipyridyl and N-acyl-N-pyridyl-N-quinoyl amine based palladium complexes. Synthesis, X-ray structures, heterogenization and use in Heck couplings", Journal of Organmetallic Chemistry, 2001, pp. 6-18, vol. 622.
File Registry on STN, 195876-33-6/RN, entered on Oct. 23, 2007.
File Registry on STN, 70125-24-5/RN, entered on Nov. 16, 1984.
Jul. 18, 2014 Office Action issued in U.S. Appl. No. 13/377,760.
Perry et al., "AIDS dementia: a review of the literature," Alzheimer Dis. Assoc. Disord. 1(4): 221-235 (1987) (PubMed Abstract 3331119).
Pauwels, "Aspects of successful drug discovery and development," Antiviral Res. 71: 77-89 (2006).
Respess et al., "Evaluation of an Ultrasensitive p24 Antigen Assay as a Potential Alternative to Human Immunodeficiency Virus Type 1 RNA Viral Load Assay in Resource-Limited Settings," J. Clin. Microbiol. 43(1): 506-08 (2005).
Aug. 15, 2014 Office Action issued in U.S. Appl. No. 13/377,753.
Dec. 5, 2014 Office Action issued in U.S. Appl. No. 14/087,762.
CAS Registry No. 215589-34-7 added on STN on Dec. 15, 1998.
CAS Registry No. 208661-32-9 added on STN on Jul. 19, 1998.
CAS Registry No. 204851-25-2 added on STN on Apr. 30, 1998.
CAS Registry No. 138386-77-3 added on STN on Jan. 17, 1992.
CAS Registry No. 70682-97-2 added on STN on Nov. 16, 1984.
CAS Registry No. 10562-04-6 added on STN on Nov. 16, 1984.
CAS Registry No. 5468-85-9 added on STN on Nov. 16, 1984.
CAS Registry No. 313266-85-2 added on STN on Jan. 9, 2001.
CAS Registry No. 294668-01-2 added on STN on Oct. 11, 2000.
CAS Registry No. 342653-87-6 added on STN on Jun. 20, 2001.
CAS Registry No. 449780-95-4 added on STN on Sep. 12, 2002.
CAS Registry No. 449780-94-3 added on STN on Sep. 12, 2002.
CAS Registry No. 324526-73-0 added on STN on Feb. 27, 2001.
Jan. 13, 2015 Russian Office Action issued in Russian Application No. 2011149572/04.

* cited by examiner

COMPOUNDS USEFUL FOR TREATING AIDS

The invention relates to novel compounds for the preparation of compositions useful for the treatment of diseases resulting from changes in splicing processes.

Certain indole derivative compounds such as ellipticine derivatives and aza-ellipticine derivatives are already known as intercalating molecules for correcting dysfunctions in gene expression, notably in DNA replication. They have been more specifically described for treating diseases such as cancer, leukemia or AIDS (see in particular patents FR 2 627 493, FR 2 645 861, FR 2 436 786).

Concerning current treatments for AIDS, the various approaches aimed at reducing viral load in patients infected by HIV utilize molecules intended to inhibit the enzymatic activity of viral reverse transcriptase or of the protease involved in virus protein maturation. Regarding reverse transcriptase inhibitors, these can be nucleosidic (NRTIs), non-nucleosidic (NNRTIs) or nucleotidic in nature. The purpose of using these compounds is to prevent a DNA copy of the retroviral genome from being produced and, consequently, from being integrated into the genome of the host cell. Protease inhibitors (PIs) interfere with the proper maturation of viral proteins and cause the production of incomplete particles with altered infectious capacities. There is another type of anti-retroviral compound used for its ability to prevent viruses from entering the cell. These entry inhibitors can be either peptides that interfere with the fusion of viral glycoproteins gp41 or gp120 with the membrane of CD4 cells or molecules that target HIV cellular co-receptors CCR5 and CXCR4. The absence of cellular proteins resembling HIV integrase has also been exploited to develop novel anti-HIV molecules that inhibit this enzymatic activity. Although a number of integrase inhibitors are in the clinical trial phase, no molecule is yet available on the market.

The intracellular splicing process consists of eliminating introns in pre-messenger RNAs to produce mature messenger RNAs that can be used by the translation mechanism of the cell (SHARP, Cell, vol. 77, p. 805-815, 1994). In the case of alternative splicing, the same precursor can be the source of messenger RNAs coding for proteins with distinct functions (BLACK, Annu. Rev. Biochem. vol. 72, p. 291-336, 2003). The precise selection of 5' and 3' splicing sites is thus a mechanism that generates diversity and that can lead to the regulation of gene expression according to the type of tissue or during the development of an organism. The factors involved in this selection include a family of proteins called SR, characterized by the presence of one or two RNA recognition motifs (RRM) and a domain rich in arginine and serine residues called an RS domain (MANLEY & TACKE, Genes Dev., vol. 10, p. 1569-1579, 1996). By binding to short exon or intron sequences of the pre-mRNA, called ESE (exonic splicing enhancer) or ISE (intronic splicing enhancer), SR proteins are able to activate, in a dose-dependant manner, sub-optimal splicing sites and to enable the inclusion of exons (GRAVELEY, RNA, vol. 6, p. 1197-1211, 2000). The activity of an SR protein in alternative splicing is specific insofar as the inactivation of the corresponding gene is lethal (WANG et al., Mol. Cell, vol. 7, p. 331-342, 2001).

Sequencing of the human genome and analysis of EST (expressed sequence tag) banks has revealed that 90-94% of genes are expressed in the form of alternatively spliced variants (Wang et al., Nature vol. 456, p. 470-474, 2008; Pan et al., Nat. Genet, vol. 40, p. 1413-1425, 2008). This mechanism is thus a favored target of modifications that can affect the factors involved in regulating splicing and of mutations that affect the sequences necessary for this regulation. At present, it is estimated that roughly 50% of the point mutations responsible for genetic diseases induce aberrant splicing. These mutations can interfere with splicing by inactivating or creating splicing sites, but also by modifying or generating regulating elements such as splicing enhancers or splicing silencers in a particular gene (CARTEGNI et al., Nat. Rev. Genet., vol. 3, p. 285-298, 2002; TAZI et al., TIBS, vol. 40, p. 469-478, 2005).

The strategies currently developed to correct these splicing defects rest on the use of various types of molecules (TAZI et al., cited above, 2005).

One strategy aimed at developing novel molecules to correct or eliminate abnormal splicing, for example, rests on the overexpression of proteins that interfere with this type of splicing (NISSIM-RAFINIA et al., Hum. Mol. Genet., vol. 9, p. 1771-1778, 2000; HOFINANN et al., Proc. Natl. Acad. Sci. U.S.A., vol. 97, p. 9618-9623, 2000).

Other strategies rest on the use of antisense oligonucleotides (SAZANI et al., Nat. Biotechnol., vol. 20, p. 1228-1233, 2002; SAZANI & KOLE, Prog. Mol. Subcell. Biol., vol. 31, p. 217-239, 2003) or of PNA (CARTEGNI et al., Nat. Struct. Biol., vol. 10, p. 120-125, 2003) enabling, respectively, the inhibition or activation of a splicing event.

Yet another strategy rests on the identification of compounds that influence the splicing efficiency of the pre-mRNA of interest (ANDREASSI et al., Hum. Mol. Genet., vol. 10, p. 2841-2849, 2001).

Lastly, a strategy based on the use of trans-splicing to replace mutant exons has been described (LIU et al., Nat. Biotechnol., vol. 20, p. 47-52, 2002).

One of the disadvantages of the developed strategies cited above to correct or eliminate abnormal splicing is their production cost. Indeed, the cost of producing antisense oligonucleotides that must be modified to improve their stability, and that of PNA molecules, is high.

Another disadvantage of the developed strategies cited above is that they require the use of expression vectors, such as, for example, for the strategy based on the use of trans-splicing.

International application WO05023255, under French priority of applications FR0310460 and FR0400973, filed by the Applicant, disclosed the use of indole derivatives to treat diseases related to the pre-messenger RNA splicing process in the cell.

Thus it was recently shown that certain indole derivatives prove particularly effective in treating metastatic cancer and in treating AIDS (BAKKOUR et al., PLoS Pathogens, vol. 3, p. 1530-1539, 2007).

However, the compounds described have a flat structure with four rings that have the disadvantage of intercalating between DNA bases and can thus lead to cellular toxicity.

In order to minimize the risk that these indole derivatives intercalate between DNA bases, the inventors developed novel compounds that are particularly effective in treating diseases related to the splicing process, but which, in a surprising manner, have a cellular toxicity that is clearly less than the indole derivatives of the prior art. In addition, these compounds are able to selectively inhibit certain splicing events.

According to a first aspect, a subject-matter of the present invention relates to a compound of formula (I) for use as an agent for preventing, inhibiting or treating AIDS

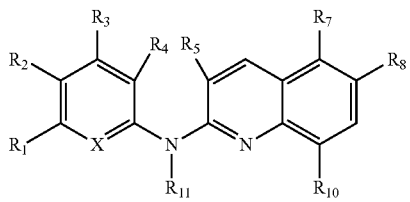
(I)

wherein:

X is $CR_0$ or N, i.e. forms together with the ring to which it belongs respectively a benzene or a pyridine group, $R_0$, $R_1$, $R_2$, $R_3$, $R_4$, $R_7$ and $R_8$ independently represent a hydrogen atom, a halogen atom or a group chosen among a $(C_1$-$C_5)$alkyl group, a $(C_3$-$C_6)$cycloalkyl group, a $(C_1$-$C_5)$ fluoroalkyl group, a $(C_1$-$C_5)$alkoxy group, a $(C_1$-$C_5)$fluoroalkoxy group, a —CN group, a —$COOR_a$ group, a —$NO_2$ group, a —$NR_aR_b$ group, a —$NR_a$—$SO_2$—$NR_aR_b$ group, a —$NR_a$—$SO_2$—$R_a$ group, a —$NR_a$—$C(=O)$—$R_a$ group, a —$NR_a$—$C(=O)$—$NR_aR_b$ group, a —$SO_2$—$NR_aR_b$ group, a —$SO_3H$ group, a —OH group, a —O—$SO_2$—$OR_c$, group, a —O—$P(=O)$—$(OR_c)(OR_d)$ group, a —O—$CH_2$—$COOR_c$, group and can further be a group chosen among:

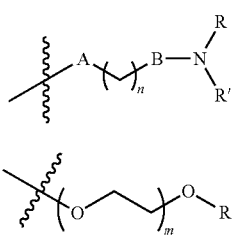
(IIa)

(IIIa)

A is a covalent bond, an oxygen atom or NH,
B is a covalent bond or NH,
n is 1, 2, 3, 4 or 5,
m is 1, 2 or 3,
R, R', $R_a$ and $R_b$ independently represent a hydrogen atom, a $(C_1$-$C_5)$alkyl group or a $(C_3$-$C_6)$cycloalkyl group, R and R' can further form together with the nitrogen atom to which they are attached a saturated 5- or 6-membered heterocycle optionally containing a further heteroatom chosen among N, O and S, said heterocycle being optionally substituted by one or more R, $R_c$ and $R_d$ independently represent a hydrogen atom, $Li^+$, $Na^+$, $K^+$, $N^+(R_a)_4$ or a benzyl group, $R_5$ represents a hydrogen atom, a $(C_1$-$C_5)$alkyl group or a $(C_3$-$C_6)$cycloalkyl group, $R_{10}$ is a hydrogen atom or a chlorine atom, and
$R_{11}$ is a hydrogen atom or a $(C_1$-$C_4)$alkyl group,
or anyone of its pharmaceutically acceptable salts, provided that at least three of $R_5$, $R_7$, $R_8$ and $R_{10}$ are different from a hydrogen atom, or alternatively provided that one of $R_7$ and $R_8$ is a group chosen among (IIa)

(IIIa)

a —$NR_a$—$SO_2$—$NR_aR_b$ group, a —$NR_a$—$SO_2$—$R_a$, group, a —$NR_a$—$C(=O)$—$R_a$ group and a —$NR_a$—$C(=O)$—$NR_aR_b$ group wherein R, R', A, B, $R_a$, $R_b$, n and m are as defined above, and the other of $R_7$ and $R_8$ is a hydrogen atom, or alternatively provided that one of $R_0$, $R_1$, $R_2$, $R_3$ and $R_4$ is a group chosen among (IIa)

(IIIa)

a —$NR_a$—$SO_2$—$NR_aR_b$ group, a —$NR_a$—$SO_2$—$R_a$ group, a —$NR_a$—$C(=O)$—$R_a$ group and a —$NR_a$—$C(=O)$—$NR_aR_b$ group wherein R, R', A, B, $R_a$, $R_b$, n and m are as defined above.

According to a further aspect, a subject-matter of the present invention relates to a compound of formula (I) as defined above, as such, or anyone of its pharmaceutically acceptable salts, and provided that the following compounds are excluded:
a compound of formula (I) wherein when $R_2$ is —OH then neither $R_1$ nor $R_3$ is a

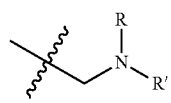

radical, wherein R and R' are as defined above,
a compound of formula (I) wherein when $R_8$ is a methoxy group then neither $R_1$ nor $R_3$ is a

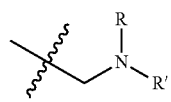

radical, wherein R and R' are as defined above,
a compound of formula (I) wherein when $R_8$ is a —NH—$C(=O)$—$CH_3$ group then $R_2$ is not a —$N(CH_3)_2$ group, and with the exclusion of the following compounds

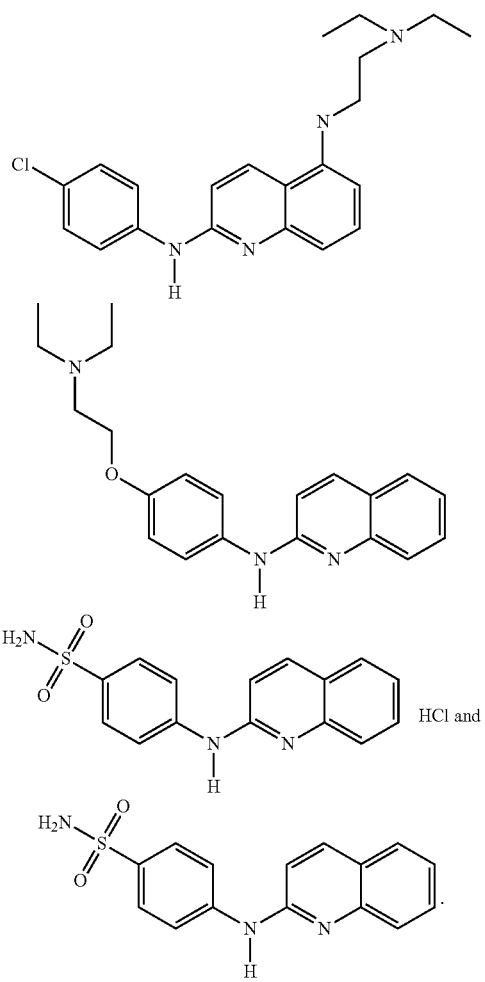

HCl and

According to a more particular embodiment, the present invention particularly focuses on a compound of formula (I), as such wherein:

X is $CR_0$ or N, i.e. forms together with the ring to which it belongs respectively a benzene or a pyridine group, $R_0$ and $R_4$ are independently a hydrogen atom, a fluorine atom, a $NO_2$ group, a $NH_2$ group, a methyl group, a methoxy group, a trifluoromethoxy group, a —N—$SO_2$—N($CH_3$)$_2$ group, a —N—$SO_2$—$CH_3$ group, a —N—C(=O)—$CH_3$ group or a —N—C(=O)—$NR_aR_b$ group, $R_1$ and $R_3$ independently represent a hydrogen atom, a methyl group or a trifluoromethyl group, a chlorine atom, a methoxy group, a trifluoromethoxy group, or a group chosen among:

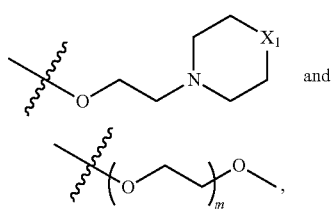

and $X_1$ is O, N($CH_3$) or $CH_2$,
m is 1 or 2, $R_2$ is a hydrogen atom, a fluorine atom, a methyl group, a trifluoromethyl group, a $NH_2$ group, a methoxy group, a trifluoromethoxy group, a —O—$CH_2$—$CH_2$—OH group, a —N—$SO_2$—N($CH_3$)$_2$ group, a —N—$SO_2$—$CH_3$ group, a —N—C(=O)—$CH_3$ group or a —N—C(=O)—$NR_aR_b$ group, $R_5$ represents a hydrogen atom or a methyl group, $R_7$ is a hydrogen atom, a $NH_2$ group, or when $R_8$ is a hydrogen atom, $R_7$ can further be a group chosen among:

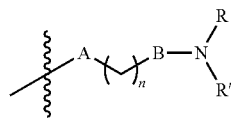

(IIa)

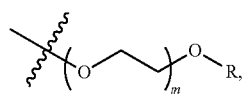

(IIIa)

a —N—$SO_2$—N($CH_3$)$_2$ group, a —N—$SO_2$—$CH_3$ group, a —N—C(=O)—$CH_3$ group and a —N—C(=O)—N($R_a$)($R_b$) group, n is 1, 2 or 3, A, B, R, R', $R_a$ and $R_b$ are as defined above in formula (I), $R_8$ is a hydrogen atom, a $NH_2$ group or when $R_7$ is a hydrogen atom, $R_8$ can further be a group chosen among:

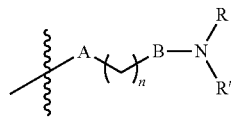

(IIa)

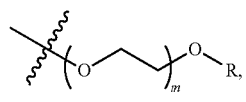

(IIIa)

$R_{10}$ is a hydrogen atom or a chlorine atom, and
$R_{11}$ is a hydrogen atom or a ($C_1$-$C_4$)alkyl group,
or anyone of its pharmaceutically acceptable salts, provided that at least three of $R_5$, $R_7$, $R_8$ and $R_{10}$ are different from a hydrogen atom, or alternatively provided that one of $R_7$ and $R_8$ is a group chosen among:

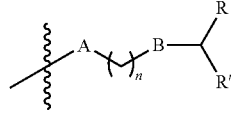

(IIa)

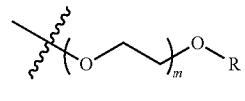

(IIIa)

and the other of $R_7$ and $R_8$ is a hydrogen atom, $R_7$ being further able to be a —N—$SO_2$N($CH_3$)$_2$ group, a —N—$SO_2$—$CH_3$ group, a —N—C(=O)—$CH_3$ group or a —N—C(=O)—$NR_aR_b$ group when $R_8$ is a hydrogen atom wherein R, R', A, B, $R_a$, $R_b$, n and m are as defined above, or alternatively provided that $R_1$ or $R_3$ is a group chosen among:

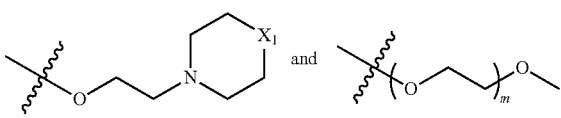

wherein $X_1$ and m are as defined above, or alternatively provided that $R_0$, $R_2$ or $R_4$ is a group chosen among a —N—SO$_2$—N(CH$_3$)$_2$ group, a —N—SO$_2$—CH$_3$ group, a —N—C(=O)—CH$_3$ group and a —N—C(=O)—NR$_a$R$_b$ group wherein $R_a$, and $R_b$ are as defined above, and provided that the following compound is excluded:

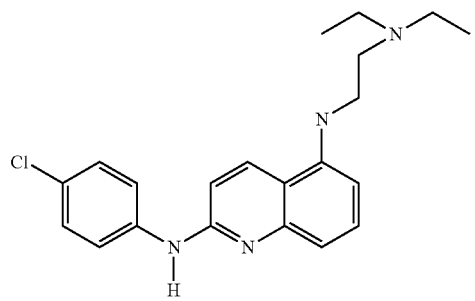 [SMILES: CCN(CC)CCNc1cccc2nc(Nc3ccc(Cl)cc3)ccc12]

According to a particular embodiment, an additional subject-matter of the present invention is a compound of formula (A1), as such

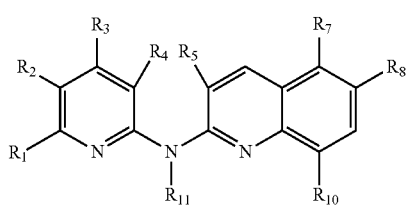

(A1)

wherein:

$R_1$ and $R_3$ independently represents a hydrogen atom, a methyl group or a trifluoromethyl group, $R_2$ is a hydrogen atom, a fluorine atom, a methyl group, a trifluoromethyl group, a NH$_2$ group, a N—SO$_2$—N(CH$_3$)$_2$ group, a —N—SO$_2$—CH$_3$ group, a —N—C(=O)—CH$_3$ group or a —N—C(=O)—NR$_a$R$_b$ group, $R_4$ is a hydrogen atom, a NO$_2$ group, a NH$_2$ group, a fluorine atom, a methyl group, a —N—SO$_2$—N(CH$_3$)$_2$ group, a —N—SO$_2$—CH$_3$ group, a —N—C(=O)—CH$_3$ group or a —N—C(=O)—NR$_a$R$_b$ group, $R_5$ is a hydrogen atom or a methyl group, $R_7$ is a hydrogen atom, a NH$_2$ group, or when $R_8$ is a hydrogen atom, $R_7$ is a group chosen among:

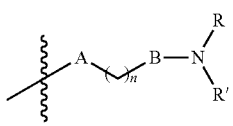

(IIa)

-continued

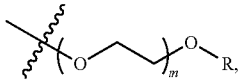

(IIIa)

a —N—SO$_2$—N(CH$_3$)$_2$ group, a —N—SO$_2$—CH$_3$ group, a —N—C(=O)—CH$_3$ group and a —N—C(=O)—NR$_a$R$_b$ group, n is 1, 2 or 3, m is 1 or 2, A, B, R, R', $R_a$, and $R_b$ are as defined above in formula (I), $R_8$ is a hydrogen atom, a NH$_2$ group, or when $R_7$ is a hydrogen atom, $R_8$ can further be a group chosen among:

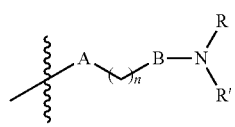

(IIa)

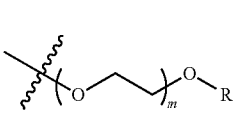

(IIIa)

$R_{10}$ is a hydrogen atom or a chlorine atom, and $R_{11}$ is as defined above in formula (I) and is advantageously a hydrogen atom, or anyone of its pharmaceutically acceptable salts, provided that at least three of $R_5$, $R_7$, $R_8$ and $R_{10}$ are different from a hydrogen atom, or alternatively provided that one of $R_7$ and $R_8$ is a group chosen among:

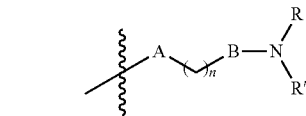

(IIa)

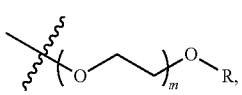

(IIIa)

and the other of $R_7$ and $R_8$ is a hydrogen atom, $R_7$ being further able to be a —N—SO$_2$—N(CH$_3$)$_2$ group, a —N—SO$_2$—CH$_3$ group, a —N—C(=O)—CH$_3$ group or a —N—C(=O)—NR$_a$R$_b$ group when $R_8$ is a hydrogen atom wherein R, R', A, B, $R_a$, $R_b$, n and m are as defined above, or alternatively provided that $R_2$ or $R_4$ is a group chosen among a —N—SO$_2$—N(CH$_3$)$_2$ group, a —N—SO$_2$—CH$_3$ group, a —N—C(=O)—CH$_3$ group and a —N—C(=O)—NR$_a$R$_b$ group wherein $R_a$ and $R_b$ are as defined above, According to another particular embodiment, an additional subject-matter of the present invention is a compound of formula (B1), as such

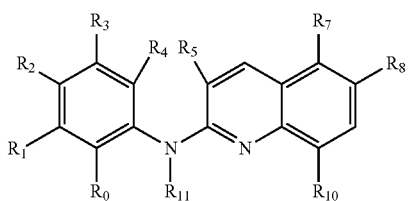

(B1)

wherein:

$R_0$ and $R_4$ are independently a hydrogen atom, a $NO_2$ group, a $NH_2$ group, a methyl group, a methoxy group, a trifluoromethoxy group, a —N—$SO_2$—N($CH_3$)$_2$ group, a —N—$SO_2$—$CH_3$ group, a —N—C(=O)—$CH_3$ group or a —N—C(=O)—$NR_aR_b$ group, $R_1$ and $R_3$ independently represent a hydrogen atom, a chlorine atom, a methoxy group, a trifluoromethoxy group, or a group chosen among:

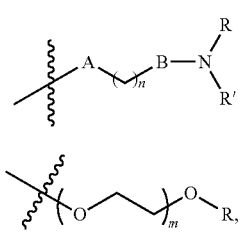

$X_1$ is O, N($CH_3$) or $CH_2$, m is 1 or 2, $R_2$ is a hydrogen atom, a methoxy group, a trifluoromethoxy group, or a —O—$CH_2$—$CH_2$—OH group, $R_5$ is a hydrogen atom or a methyl group, $R_7$ is a hydrogen atom, a $NH_2$ group, or when $R_8$ is a hydrogen atom, $R_7$ is a group chosen among:

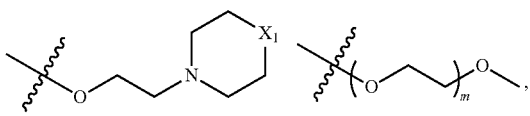

(IIa)

(IIIa)

a —N—$SO_2$—N($CH_3$)$_2$ group, a —N—$SO_2$—$CH_3$ group, a —N—C(=O)—$CH_3$ group and a —N—C(=O)—$NR_aR_b$ group, n is 1, 2 or 3, A, B, R, R', $R_a$ and $R_b$ are as defined above in formula (I), $R_8$ is a hydrogen atom, a $NH_2$ group or when $R_7$ is a hydrogen atom, $R_8$ can further be a group chosen among:

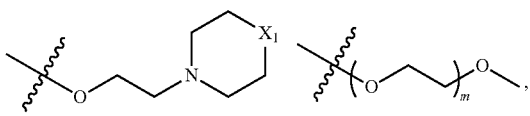

(IIa)

(IIIa)

$R_{10}$ is a hydrogen atom or a chlorine atom, and $R_{11}$ is as defined above in formula (I) and is advantageously a hydrogen atom, or anyone of its pharmaceutically acceptable salts, provided that at least three of $R_5$, $R_7$, $R_8$ and $R_{10}$ are different from a hydrogen atom, or alternatively provided that one of $R_7$ and $R_8$ are a group chosen among:

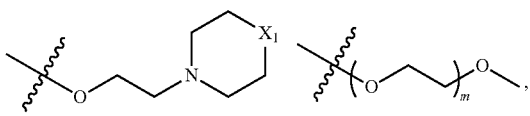

(IIa)

(IIIa)

and the other or $R_7$ and $R_8$ is a hydrogen atom, $R_7$ being further able to be a —N—$SO_2$—N($CH_3$)$_2$ group, a —N—$SO_2$—$CH_3$ group, a —N—C(=O)—$CH_3$ group or a —N—C(=O)—$NR_aR_b$ group, when $R_8$ is a hydrogen atom wherein R, R', A, B, $R_a$, $R_b$, n and m are as defined above, or alternatively provided that $R_1$ or $R_3$ is a group chosen among:

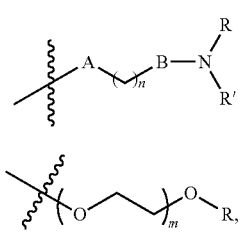

wherein $X_1$ and m are as defined above, or alternatively provided that $R_0$, $R_2$ or $R_4$ is a group chosen among a —N—$SO_2$—N($CH_3$)$_2$ group, a —N—$SO_2$—$CH_3$ group, a —N—C(=O)—$CH_3$ group and a —N—C(=O)—$NR_aR_b$ group wherein $R_a$ and $R_b$ are as defined above, and provided that the following compound is excluded:

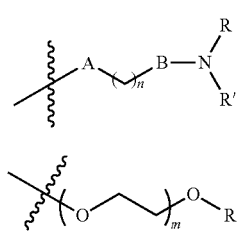

According to a more particular embodiment, the present invention particularly focuses on a compound of formula (A1), as such wherein:

$R_1$, $R_2$, $R_8$ and $R_{11}$ are a hydrogen atom, $R_3$ is a methyl group or a trifluoromethyl group, $R_4$ is a hydrogen atom or a $NH_2$ group, $R_5$ is a hydrogen atom or a methyl group, $R_7$ is a hydrogen atom, a $NH_2$ group, or when $R_8$ is a hydrogen atom, $R_7$ can further be a group chosen among:

and a —N—SO$_2$—N(CH$_3$)$_2$ group, n' is 0, 1, or 2 and more preferably 1, and R$_{10}$ is a hydrogen atom or a chlorine atom, or anyone of its pharmaceutically acceptable salts, provided that at least three of R$_5$, R$_7$, R$_8$ and R$_{10}$ are different from a hydrogen atom, or alternatively provided that R$_7$ is a group chosen among:

and a —N—SO$_2$—N(CH$_3$)$_2$ group wherein n' is as defined above.

Still according to this more particular embodiment, the present invention more particularly focuses on compounds of formula (A1'), as such (A1')

wherein:

R$_3$ is a hydrogen atom, a methyl group or a trifluoromethyl group, and is advantageously a methyl group or a trifluoromethyl group, R$_4$ is a hydrogen atom, a NO$_2$ group, a NH$_2$ group, a fluorine atom, a methyl group, a —N—SO$_2$—N(CH$_3$)$_2$ group, —N—SO$_2$—CH$_3$ group, a —N—C(=O)—CH$_3$ group or a —N—C(=O)—NR$_a$R$_b$ group, and is advantageously a hydrogen atom or a NH$_2$ group, R$_5$ is a hydrogen atom or a methyl group, R$_7$ is a hydrogen atom, a NH$_2$ group, or a group chosen among:

(IIa)

(IIIa)

a —N—SO$_2$—N(CH$_3$)$_2$ group, a —N—SO$_2$—CH$_3$ group, a —N—C(=O)—CH$_3$ group and a —N—C(=O)—NR$_a$R$_b$ group, and is advantageously a —N—SO$_2$—N(CH$_3$)$_2$ group, a NH$_2$ group or a group chosen among:

n is 1, 2 or 3, and is advantageously 2, n' is 0, 1 or 2 and is advantageously 1, m is 1 or 2, A, B, R, R', R$_a$ and R$_b$ are as defined above in formula (I), and R$_{11}$ is as defined above in formula (I) and is advantageously a hydrogen atom, or anyone of its pharmaceutically acceptable salts, provided that R$_5$ and R$_7$ are not hydrogen atom, or alternatively provided that R$_5$ is a hydrogen atom and R$_7$ is chosen among (IIa)

(IIIa)

a —N—SO$_2$—N(CH$_3$)$_2$ group, a —N—SO$_2$—CH$_3$ group, a —N—C(=O)—CH$_3$ group and a —N—C(=O)—NR$_a$R$_b$ group wherein R, R', A, B, R$_a$, R$_b$, n and m are as defined above, or alternatively provided that R$_7$ is a hydrogen atom and R$_4$ is chosen among a —N—SO$_2$—N(CH$_3$)$_2$ group, —N—SO$_2$—CH$_3$ group, a —N—C(=O)—CH$_3$ group and a —N—C(=O)—NR$_a$R group wherein R$_a$ and R$_b$ are as defined above.

According to another more particular embodiment, the present invention particularly focuses on a compound of formula (B1), as such wherein:

R$_0$, R$_1$, R$_4$, R$_8$ and R$_{11}$ are independently a hydrogen atom,

R$_2$ is a methoxy group, a trifluoromethoxy group or a —O—CH$_2$—CH$_2$—OH group, R$_3$ is a hydrogen atom, a chlorine atom, or a group chosen among:

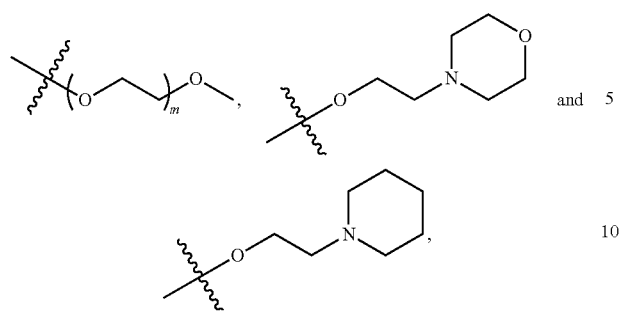 and

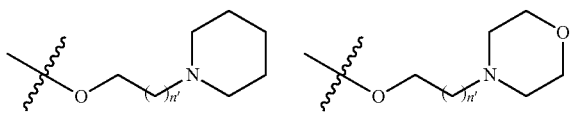, m is 1 or 2 and more preferably 2, $R_5$ is a hydrogen atom or a methyl group, $R_7$ is a hydrogen atom, a $NH_2$ group, or when $R_8$ is a hydrogen atom, $R_7$ can further be a group chosen among:

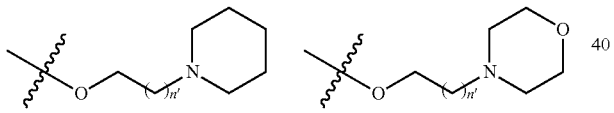

and a —NH—SO$_2$—N(CH$_3$)$_2$ group, n' is 0, 1, or 2, and more preferably 1, and $R_{10}$ is a hydrogen atom or a chlorine atom, or anyone of its pharmaceutically acceptable salts, provided that at least three of $R_5$, $R_7$, $R_8$ and $R_{00}$ are different from a hydrogen atom, or alternatively provided that $R_7$ is a group chosen among:

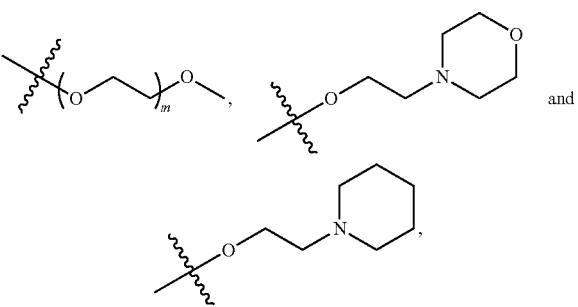

and a —N—SO$_2$—N(CH$_3$)$_2$ group wherein n' is as defined above, or alternatively provided that $R_3$ is a group chosen among:

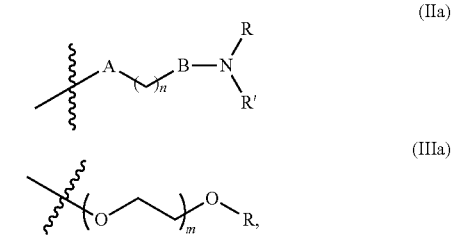

wherein m is as defined above.

Still according to this more particular embodiment, the present invention more particularly focuses on compounds of formula (B1'), as such

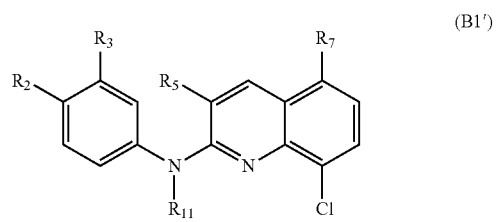

wherein:

$R_2$ is a hydrogen atom, a methoxy group, a trifluoromethoxy group, or a —O—CH$_2$—CH$_2$—OH group and is advantageously a methoxy group, a trifluoromethoxy group, or a —O—CH$_2$—CH$_2$—OH group, $R_3$ is a hydrogen atom, a chlorine atom, a methoxy group, a trifluoromethoxy group, or a group chosen among:

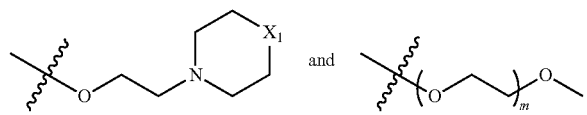 and

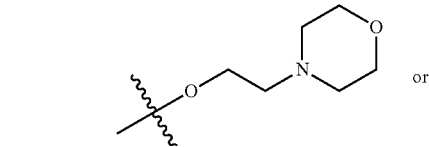

and is advantageously a chlorine atom, a hydrogen atom, a —O—CH$_2$—CH$_2$—O—CH$_2$—CH$_2$—O—CH$_3$ group,

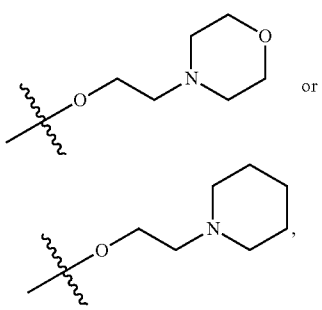 or $X_1$ is O, N(CH$_3$) or CH$_2$ and is advantageously O or CH$_2$, m is 1 or 2 and is advantageously 2, $R_5$ is a hydrogen atom or a methyl group, $R_7$ is a hydrogen atom, a $NH_2$ group, or when $R_8$ is a hydrogen atom, $R_7$ is a group chosen among:

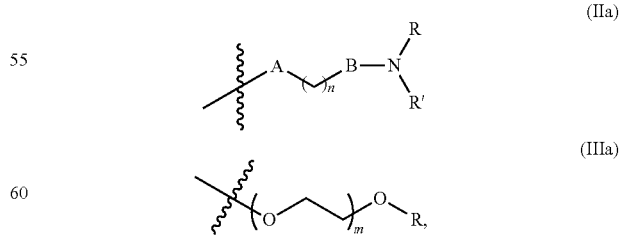

a —N—SO$_2$—N(CH$_3$)$_2$ group, a —N—SO$_2$—CH$_3$ group, a —N—C(=O)—CH$_3$ group and a —N—C(=O)—NR$_a$R$_b$ group and is advantageously a hydrogen atom, a NH$_2$ group, a —NH—SO$_2$—N(CH$_3$)$_2$ group, or a group chosen among

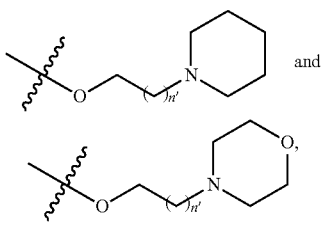

n' is 0, 1, or 2, and more preferably 1,
n is 1, 2 or 3, and is advantageously 2,
R, R', A, B, $R_a$ and $R_b$ are as defined above in formula (I), and
$R_{11}$ is as defined above in formula (I) and is advantageously a hydrogen atom,
or anyone of its pharmaceutically acceptable salts,
provided that $R_5$ and $R_7$ are not a hydrogen atom, or alternatively
provided that $R_5$ is a hydrogen atom and $R_7$ is a group chosen among:

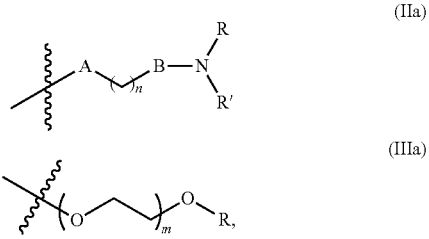

a —N—SO$_2$—N(CH$_3$)$_2$ group, a —N—SO$_2$—CH$_3$ group, a —N—C(O)—CH$_3$ group and a —N—C(=O)—NR$_a$R$_b$ group wherein R, R', A, B, $R_a$, $R_b$, n and m are as defined above, or alternatively
provided that $R_7$ is a hydrogen atom and $R_3$ is a group chosen among:

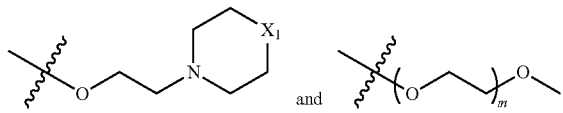

and wherein $X_1$ and m are as defined above.

In a preferred embodiment, in the above defined compounds of formulae (I), (A1), (B1), (A1') and (B1'), the group of formula (IIa) is a group chosen among:

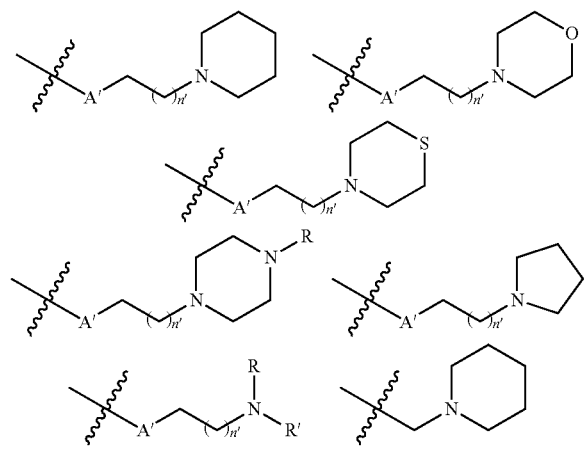

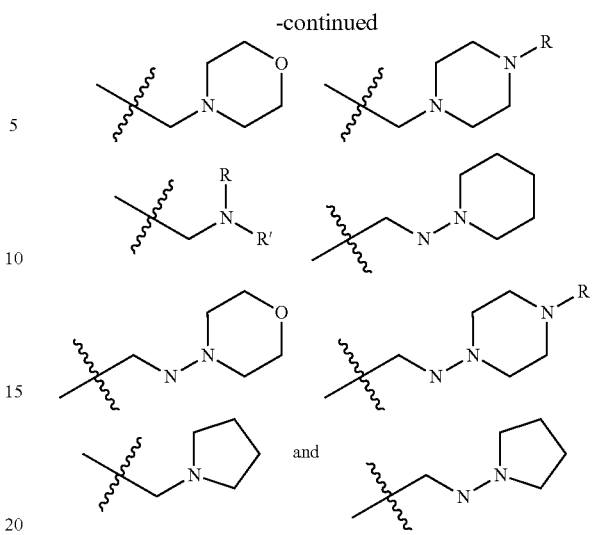

wherein A' is O or NH, n' is 0, 1, 2, 3, or 4 and R and R' are as defined above in formulae (I), (A1), (B1), (A1') and (B1'). Preferably, in the $R_8$ position, the radical A' is O.

According to a preferred embodiment of the present invention, the novel compound of formula (I), is chosen from:

(1)  8-chloro-5-(2-morpholinoethoxy)-N-(4-(trifluoromethyl)pyridin-2-yl)quinolin-2-amine
(2)  N2-(8-chloro-5-(2-morpholinoethoxy)quinolin-2-yl)-4-methylpyridine-2,3-diamine
(3)  8-chloro-5-(2-(piperidin-1-yl)ethoxy)-N-(4-(trifluoromethyl)pyridin-2-yl)quinolin-2-amine
(4)  8-chloro-3-methyl-5-(2-(piperidin-1-yl)ethoxy)-N-(4-(trifluoromethyl)pyridin-2-yl)quinolin-2-amine
(5)  N2-(8-chloro-3-methyl-5-(2-(piperidin-1-yl)ethoxy)quinolin-2-yl)-4-methylpyridine-2,3-diamine
(6)  N,N-dimethyl-N'-[2-[(4-trifluoromethylpyridin-2-yl)amino]-8-chloro-5-quinolinyl]sulfamide
(7)  N,N-dimethyl-N'-[2-[(4-trifluoromethylpyridin-2-yl)amino]-3-methyl-5-quinolinyl]sulfamide
(8)  8-chloro-3-methyl-N2-(4-(trifluoromethyl)pyridin-2-yl)quinoline-2,5-diamine
(9)  N,N-dimethyl-N'-[2-[(4-trifluoromethyl-pyridin-2-yl)amino]-8-chloro-3-methyl-5-quinolinyl]sulfamide
(10)  N'-[2-[(3-amino-4-methylpyridin-2-yl)amino]-8-chloro-5-quinolinyl]N,N-dimethylsulfamide
(11)  N'-[2-[(3-amino-4-methylpyridin-2-yl)amino]-8-chloro-3-methyl-5-quinolinyl]-N,N-dimethylsulfamide
(12)  N2-(3-amino-4-methylpyridin-2-yl)-8-chloro-3-methylquinoline-2,5-diamine
(13)  N'-[2-[(-3-amino-4-methylpyridin-2-yl)amino]-3-methyl-5-quinolinyl]-N,N-dimethylsulfamide
(26)  N-[3-methyl-2-[(4-trifluoromethylpyridin-2-yl)amino]-5-quinolinyl]-methanesulfonamide
(14)  8-chloro-5-(2-(piperidin-1-yl)ethoxy)-N-(4-(trifluoromethoxy)phenyl)quinolin-2-amine
(15)  8-chloro-3-methyl-5-(2-(piperidin-1-yl)ethoxy)-N-(4-(trifluoromethoxy)phenyl)quinolin-2-amine
(16)  8-chloro-N-(3-chloro-4-(trifluoromethoxy)phenyl)-5-(2-(piperidin-1-yl)ethoxy)quinolin-2-amine
(17)  8-chloro-N-(3-chloro-4-methoxyphenyl)-5-(2-morpholinoethoxy)quinolin-2-amine
(18)  8-chloro-N2-(3-chloro-4-(trifluoromethoxy)phenyl)-3-methylquinoline-2,5-diamine
(19)  N'-[2-[(3-chloro-4-(trifluoromethoxy)phenyl)amino]-3-methyl-5-quinolinyl]-N,N-dimethylsulfamide

(20) N-[2-[(3-chloro-4-(trifluoromethoxy)phenyl)amino]-8-chloro-5-quinolinyl]-N,N-dimethylsulfamide
(21) N'-[2-[(3-chloro-4-(trifluoromethoxy)phenyl)amino]-8-chloro-3-methyl-5-quinolinyl]-N,N-dimethylsulfamide
(22) 2-(4-((8-chloroquinolin-2-yl)amino)phenoxy)ethanol
(23) 8-chloro-N-(4-methoxy-3-(2-morpholinoethoxy)phenyl)quinolin-2-amine
(24) 8-chloro-N-(4-methoxy-3-(2-(2-methoxyethoxy)ethoxy)phenyl)quinolin-2-amine
(25) 8-chloro-N-(4-methoxy-3-(2-(piperidin-1-yl)ethoxy)phenyl)quinolin-2-amine
(27) N-[2-[(3-chloro-4-(trifluoromethoxy)phenyl)amino]-3-methyl-5-quinolinyl]-methanesulfonamide
and their pharmaceutically acceptable salts.

The present invention therefore extends to compounds (1) to (27) and their pharmaceutically acceptable salts, such as hydrobromide, tartrate, citrate, trifluoroacetate, ascorbate, hydrochloride, tartrate, triflate, maleate, mesylate, formate, acetate and fumarate.

According to another aspect, a subject-matter of the present invention relates to a compound of formula (I), (A1), (A1'), (B1) and (B1') wherein X, $R_1$, $R_2$, $R_3$, $R_4$, $R_5$, $R_7$, $R_8$, and $R_{10}$ are as defined above in compounds of formula (I), (A1), (A1'), (B1), and (B1') or anyone of its pharmaceutically acceptable salts, and anyone of compounds (1) to (27) or anyone of its pharmaceutically acceptable salts, for use as a medicament.

According to another aspect, a subject-matter of the present invention relates to a compound of formula (I), (A1), (A1'), (B1) and (B1') as defined above or anyone of its pharmaceutically acceptable salts, and anyone of compounds (1) to (27) or anyone of its pharmaceutically acceptable salts, for use as an agent for preventing, inhibiting or treating AIDS.

The term "preventing", as used herein, means reducing the risk of onset or slowing the occurrence of a given phenomenon, namely in the present invention, a disease resulting from at least one splicing anomaly such as AIDS.

The compounds of the invention may exist in the form of free bases or of addition salts with pharmaceutically acceptable acids.

Suitable physiologically acceptable acid addition salts of compounds of formula (I) include hydrobromide, tartrate, citrate, trifluoroacetate, ascorbate, hydrochloride, tartrate, triflate, maleate, mesylate, formate, acetate and fumarate.

The compounds of formula (I), (A1), (A1'), (B1) and (B1') and or salts thereof may form solvates or hydrates and the invention includes all such solvates and hydrates.

The terms "hydrates" and "solvates" simply mean that the compounds (1) according to the invention can be in the form of a hydrate or solvate, i.e. combined or associated with one or more water or solvent molecules. This is only a chemical characteristic of such compounds, which can be applied for all organic compounds of this type.

In the context of the present invention, the term:
"halogen" is understood to mean chlorine, fluorine, bromine, or iodine, and in particular denotes chlorine, fluorine or bromine,
"($C_1$-$C_5$)alkyl" as used herein respectively refers to $C_1$-$C_5$ normal, secondary or tertiary saturated hydrocarbon. Examples are, but are not limited to, methyl, ethyl, 1-propyl, 2-propyl, butyl, pentyl,
"($C_3$-$C_6$)cycloalkyl" as used herein respectively refers to cyclic saturated hydrocarbon. Examples are, but are not limited to cyclopropyl, cyclobutyl, cyclopentyl, cyclohexyl,
"($C_1$-$C_5$)alkoxy" as used herein respectively refers to O—($C_1$-$C_5$)alkyl moiety, wherein alkyl is as defined above. Examples are, but are not limited to, methoxy, ethoxy, 1-propoxy, 2-propoxy, butoxy, pentoxy,
"fluoroalkyl group" and "fluoroalkoxy group" refers respectively to alkyl group and alkoxy group as above-defined, said groups being substituted by at least one fluorine atom. Examples are perfluoroalkyl groups, such as trifluoromethyl or perfluoropropyl,
"saturated 5- or 6-membered heterocycle" as used herein respectively refers to a saturated cycle comprising at least one heteroatom. Examples are, but are not limited to, morpholine, piperazine, thiomorpholine, piperidine, pyrrolidine,
"patient" may extend to humans or mammals, such as cats or dogs.

The compounds of formulae (I), (A1), (A1'), (B1) and (B1') can comprise one or more asymmetric carbon atoms. They can thus exist in the form of enantiomers or of diastereoisomers. These enantiomers, diastereoisomers and their mixtures, including the racemic mixtures, are encompassed within the scope of the present invention.

According to another aspect, a subject-matter of the present invention relates to a compound, as such, chosen among:

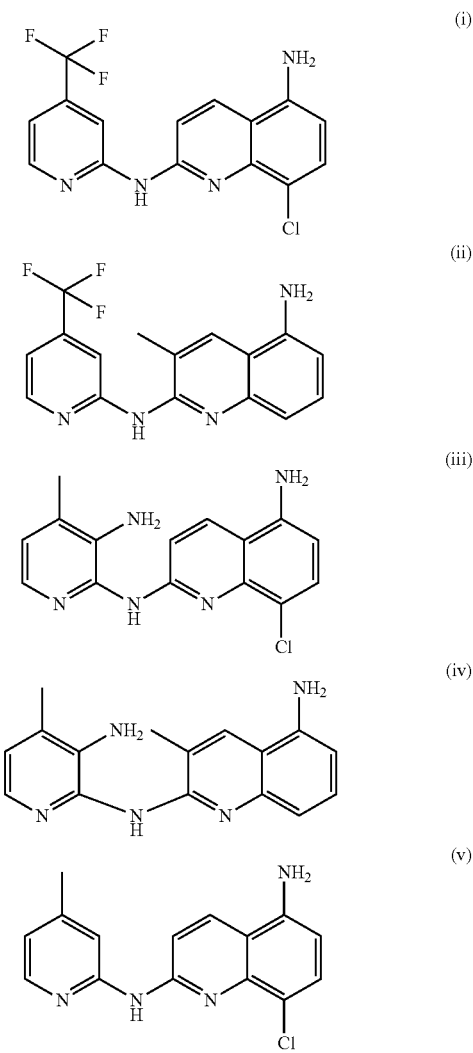

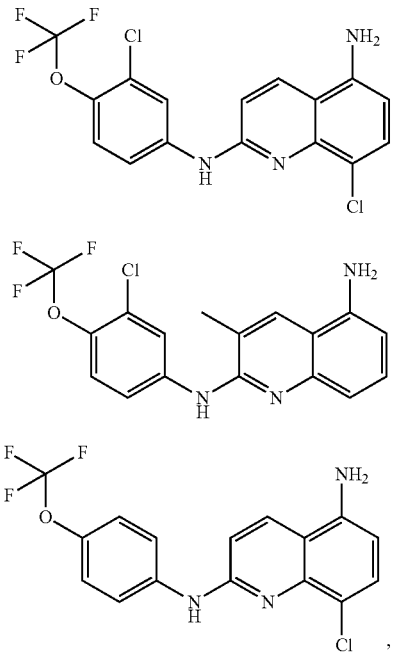

(vi)

(vii)

(viii)

or anyone of its pharmaceutically acceptable salts, such as hydrobromide, tartrate, citrate, trifluoroacetate, ascorbate, hydrochloride, tartrate, triflate, maleate, mesylate, formate, acetate and fumarate.

According to another aspect, a subject-matter of the present invention relates to a compound (i), (ii), (iii), (iv), (v), (vi), (vii) or (viii) or anyone of its pharmaceutically acceptable salts, for use as a medicament.

According to another aspect, a subject-matter of the present invention relates to a compound (i), (ii), (iii), (iv), (v), (vi), (vii) or (viii) or anyone of its pharmaceutically acceptable salts, for use as an agent for inhibiting, preventing or treating AIDS.

The new compounds of the present invention, i.e. compounds of formulae (I), (A1), (B1), (A1') and (B1'), anyone of compounds (1) to (27) or anyone of its pharmaceutically acceptable salts, and the specific compounds of formulae (i), (ii), (iii), (iv), (v), (vi), (vii) or (viii), are not only useful as agent for inhibiting, preventing or treating AIDS but can also be useful for inhibiting, preventing or treating premature aging and for inhibiting, preventing or treating cancer, and more particularly colorectal cancer, pancreatic cancer, lung cancer including non-small cell lung cancer, breast cancer, bladder cancer, gall bladder cancer, liver cancer, thyroid cancer, melanoma, uterine/cervical cancer, oesophageal cancer, kidney cancer, ovarian cancer, prostate cancer, head and neck cancer and stomach cancer, etc.

According to an aspect of the invention said compounds may be useful to inhibit, prevent and/or treat diseases with premature aging and that are likely related to an aberrant splicing of the nuclear lamin A gene. Among all, said disease may include Hutchinson Guilford Progeria Syndrome (HGPS), progeria, premature aging associated with HIV infection, muscular dystrophy, Charcot-Marie-Tooth disorder, Werner syndrome, but also atherosclerosis, insulin resistant type II diabetes, cataracts, osteoporosis and aging of the skin such as restrictive dermopathy.

The compounds of the present invention can be prepared by conventional methods of organic synthesis practiced by those skilled in the art. The general reaction sequences outlined below represent a general method useful for preparing the compounds of the present invention and are not meant to be limiting in scope or utility.

The compounds of general formula (I) can be prepared according to scheme 1 below.

As appears in said scheme two routes are available for recovering a compound of formula (I) according to the present invention.

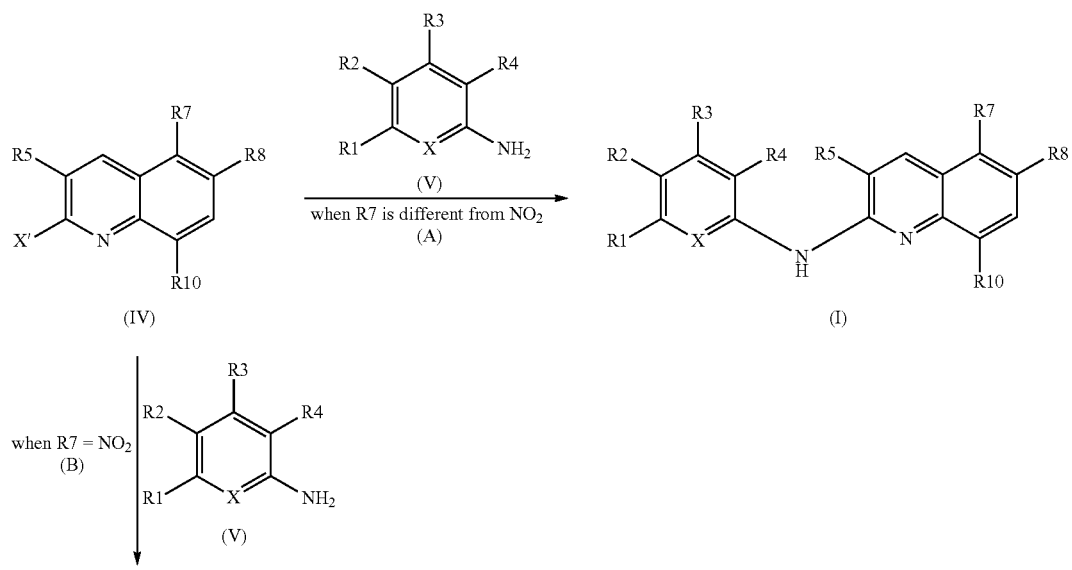

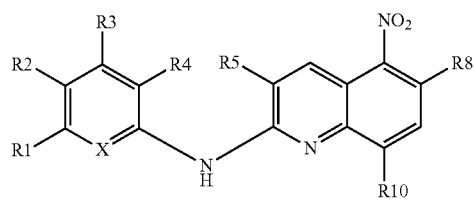

(VI)

↓

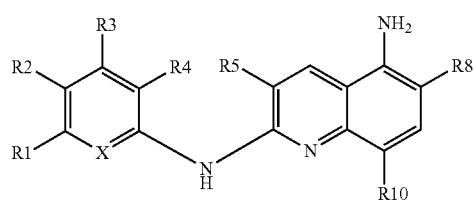

(VII)

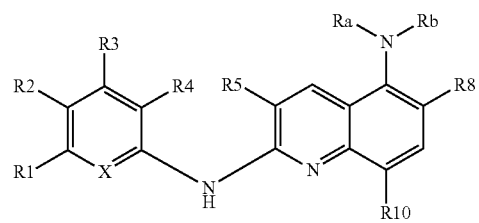

(I)

Route (A) is carried out from compound of formula (IV) wherein $R_5$, $R_7$, $R_8$ and $R_{10}$ are as defined above, X' is a chlorine atom or a bromine atom, and $R_7$ is different from —$NO_2$ in order to obtain a compound of formula (I) wherein $R_1$, $R_2$, $R_3$, $R_4$, $R_5$, X, $R_7$, $R_8$ and $R_{10}$ are as defined above and $R_7$ is different from —$NO_2$ or —$NR_aR_b$ wherein $R_a$ and $R_b$ are as defined above.

Route (B) is performed from compound of formula (IV) wherein $R_5$, $R_8$ and $R_{10}$ are as defined above, X' is a chlorine atom or a bromine atom, and $R_7$ is —$NO_2$ in order to obtain a compound of formula (I) wherein $R_1$, $R_2$, $R_3$, $R_4$, $R_5$, X, $R_8$ and $R_{10}$ are as defined above and $R_7$ is —$NO_2$ or —$NR_aR_b$ wherein $R_a$, and $R_b$ are as defined above.

According to route (A), a compound of formula (IV) is placed in a protic solvent such as tert-butanol. A compound of formula (V) wherein $R_1$, $R_2$, $R_3$, $R_4$, and X are as defined above is then added in a molar ratio ranging from 1 to 1.5 with respect to the compound of formula (IV) in presence of an inorganic base, such as $Cs_2CO_3$ or $K_2CO_3$ in a molar ratio ranging from 1 and 2, in the presence of a diphosphine, such as Xantphos (4,5-Bis(diphenylphosphino)-9,9-dimethylxanthene) or X-Phos (2-Dicyclohexylphosphino-2',4',6'-triisopropylbiphenyl) in an amount ranging from 2 mol % to 10 mol % relative to the total amount of compound of formula (IV), and in the presence of a catalyst, such as $Pd(OAc)_2$ or $Pd_2dba_3$ in an amount ranging from 2 mol % and 10 mol % relative to the total amount of compound of formula (IV). The reaction mixture can then be heated at a temperature ranging from 80 to 120° C., for example at 90° C. and stirred for a time ranging from 15 to 25 hours, for example during 20 hours under inert gas and for example argon. The reaction mixture can be concentrated under reduced pressure and the residue can be diluted with an organic solvent such as ethyl acetate. The organic phase can be washed with water, decanted and dried over magnesium sulphate. Finally, solid can be dried under vacuum overnight to give a compound of formula (I), or a compound of formula (VI) wherein $R_1$, $R_2$, $R_3$, $R_4$, $R_5$, X, $R_5$ and $R_{10}$ are as defined above. When $R_0$ or $R_1$ or $R_2$ or $R_3$ or $R_4$ is —$NO_2$, then a reduction step may be carried out as described in route (B) below.

The starting compounds of formula (IV) and (V) are available or can be prepared according to methods known to the person skilled in the art.

According to route (B), a compound of formula (VI) and tin (II) chloride dihydrate in a ratio ranging from 3 to 8 equivalents are placed in a protic solvent such as ethanol. The reaction mixture can then be heated at a temperature ranging from 40 to 80° C., for example at 60° C. and stirred for a time ranging from 15 to 25 hours, for example during 20 hours. The reaction mixture can then be concentrated under reduced pressure and the resulting residue can be diluted with an organic solvent such as ethyl acetate. The organic phase can be washed with a 1N NaOH aqueous solution, dried over magnesium sulphate, filtered and concentrated under reduced pressure to give a compound of formula (VII) wherein $R_1$, $R_2$, $R_3$, $R_4$, $R_5$, X, $R_5$ and $R_{10}$ are as defined above.

In order to obtain a compound of formula (IV) wherein $R_7$ is a nitro group, i.e. a compound of formula (IVb) wherein $R_5$, $R_8$ and $R_{10}$ are as defined above, the reactions described in scheme 2 can be performed.

Scheme 2

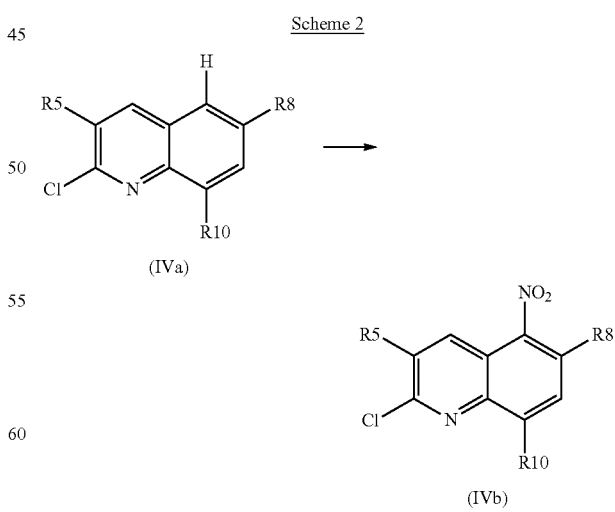

According to scheme 2, a compound of formula (IVa) wherein $R_5$, $R_8$ and $R_{10}$ are as defined above, can be placed in sulphuric acid. A mixture of nitric acid in a ratio ranging from 3 to 8 equivalents, for example 6, and sulfuric acid in a ratio ranging from 1 to 4 equivalents, for example 2, can be added at 0° C. The reaction mixture can then be heated at a temperature ranging from 30 to 80° C., for example at 40° C. and stirred for a time ranging from 15 to 60 minutes, for example during 30 minutes. Water can then be added and the solid can be collected by filtration and dried to give a compound of formula (IVb).

In order to obtain compounds of formula (IV), the following sequence of reactions may be carried out as shown in scheme 3 below.

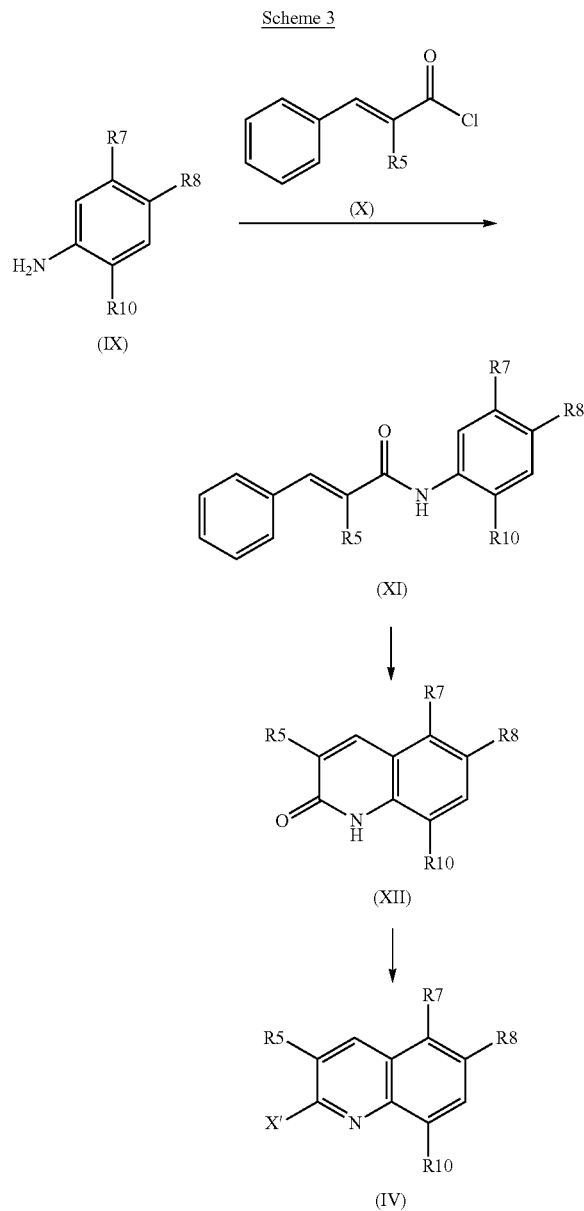

The compound of formula (IX) wherein $R_7$, $R_8$ and $R_{10}$ are as defined above, can be placed in a mixture of acetone and water in presence of an inorganic base, such as $Cs_2CO_3$ or $K_2CO_3$ in a molar ratio ranging from 1 to 2. At 0° C., the compound of formula (X) wherein $R_5$ is as defined above, can then be added in a molar ratio ranging from 1 to 1.5 with respect to the compound of formula (IX). The reaction mixture can be allowed to warm-up to room temperature and be stirred for a time ranging from 2 hours to 18 hours, for example during 18 hours. The reaction mixture can be extracted with an organic solvent such as ethylacetate. The organic phase can be decanted, dried over magnesium sulphate, filtered and concentrated under reduced pressure to afford a compound of formula (XI) wherein $R_5$, $R_7$, $R_8$ and $R_{10}$ are as defined above.

The compound of formula (XI) can be placed in an aprotic solvent such as chlorobenzene in presence of aluminium trichloride in a molar ratio ranging from 5 and 10, for example 6. The reaction mixture can then be heated at a temperature ranging from 100 to 150° C., for example at 125° C., and stirred for a time ranging from 1 to 4 hours, for example during 2 hours. The reaction mixture can be diluted with a water and ice mixture and extracted with an organic solvent such as ethyl acetate. The organic phase can be decanted, dried over magnesium sulphate, filtered and concentrated under reduced pressure to a compound of formula (XII) wherein $R_5$, $R_7$, $R_8$ and $R_{10}$ are as defined above.

The compound of formula (XII) can be placed in an aprotic solvent such as acetonitrile in presence of $POCl_3$ in a molar ratio ranging from 2 to 10, for example 5, and in presence of triethylbenzylammonium chloride in a molar ratio ranging from 2 to 10, for example 5. The reaction mixture can then be heated at a temperature ranging from 100 to 120° C., for example at 120° C. and stirred for a time ranging from 1 to 4 hours, for example during 3 hours. The mixture can then be concentrated under reduced pressure and, after adding water to the residue, can be stirred at room temperature for a time ranging from 15 to 60 minutes, for example during 30 minutes. The resulting precipitate can then be washed with water and filtered to give a compound of formula (IV).

A compound of formula (V) (Scheme 1) or a compound of formula (IX) (Scheme 3) with a chain connected by an oxygen atom to the aromatic ring, may be obtained according to scheme 4 as shown below.

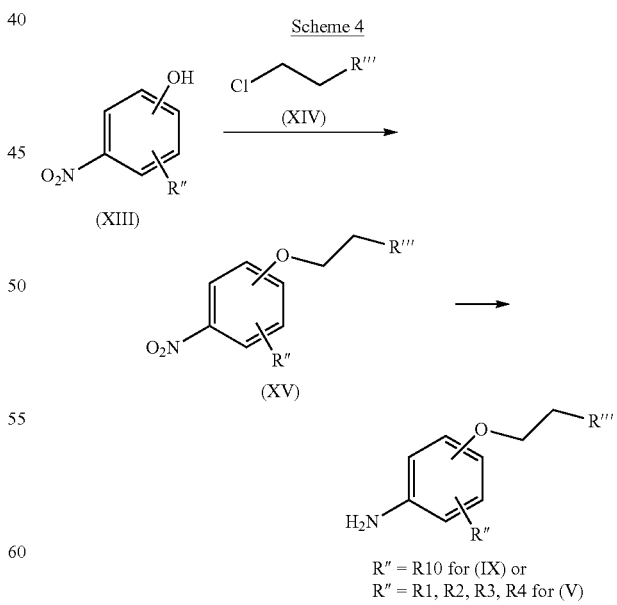

R″ = R10 for (IX) or
R″ = R1, R2, R3, R4 for (V)

The compound of formula (XIII) wherein R″ is as defined above in scheme 4, can be placed in a polar solvent such as N,N-dimethylformamide. The compound of formula (XIV) wherein R‴ is —(O—$CH_2$—$CH_2$)$_f$—O—R or —B—NRR′, f is 0, 1 or 2 and B, R and R' are as defined above, can then be added in a molar ratio ranging from 1 to 1.5 with respect to the compound of formula (XIII) in presence of an inorganic base, such as $Cs_2CO_3$ or $K_2CO_3$ in a molar ratio ranging from 1 to 2 and in the presence of potassium iodide in a ratio ranging from 1.5 to 3 for example 2.2 equivalents. The reaction mixture can then be heated at a temperature ranging from 60 to 100° C., for example at 80° C. and stirred for a time ranging from 15 to 25 hours, for example during 20 hours. The reaction mixture can then be concentrated under reduced pressure and the resulting residue can be diluted with an organic solvent such as ethyl acetate. The organic phase can be washed with a 1% NaOH aqueous solution, dried over magnesium sulphate, filtered and concentrated under reduced pressure to give a compound of formula (XV) wherein R" and R'" are as defined above.

The compound of formula (XV) and tin (II) chloride dihydrate in a ratio ranging from 3 to 8 equivalents can be placed in a protic solvent such as ethanol. The reaction mixture can then be heated at a temperature ranging from 40 to 80° C., for example at 60° C. and stirred for a time ranging from 15 to 25 hours, for example during 20 hours. The reaction mixture can then be concentrated under reduced pressure and the resulting residue can be diluted with an organic solvent such as ethyl acetate. The organic phase can be washed with a 1N NaOH aqueous solution, dried over magnesium sulphate, filtered and concentrated under reduced pressure to give a compound of formula (V) or (IX).

The chemical structures and spectroscopic data of some compounds of formula (I) of the invention are illustrated respectively in the following Table I and Table II.

TABLE I

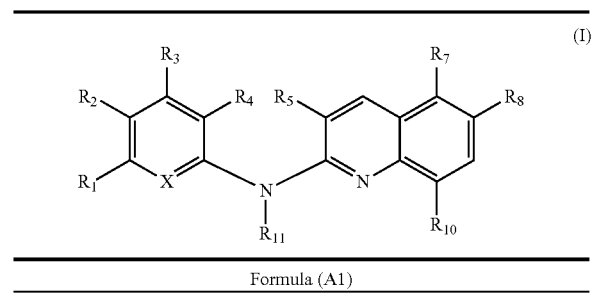

Formula (A1)

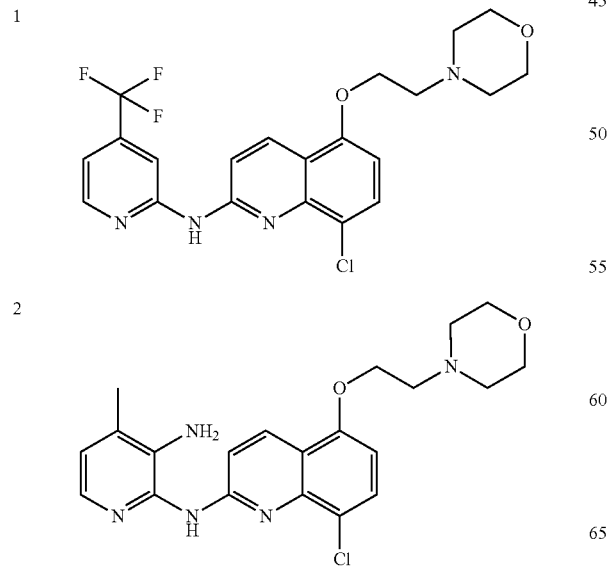

TABLE I-continued

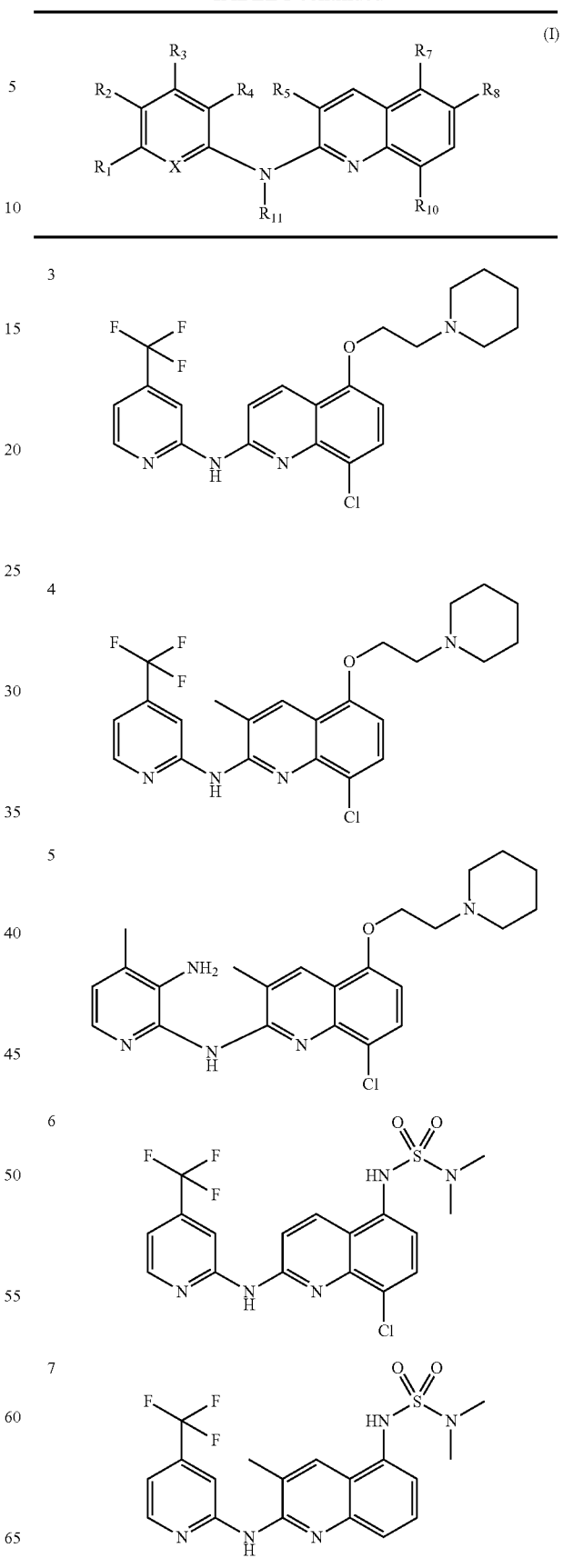

TABLE I-continued
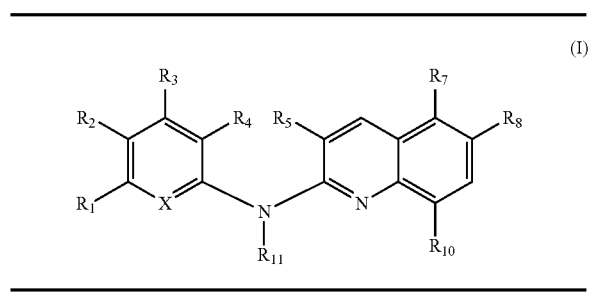
| 8 | 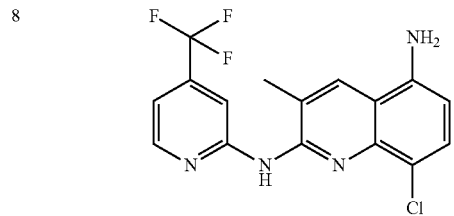 |
|---|---|
| 9 | 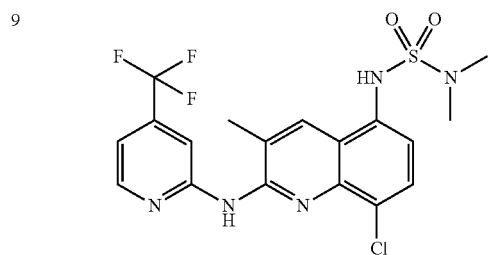 |
| 10 | 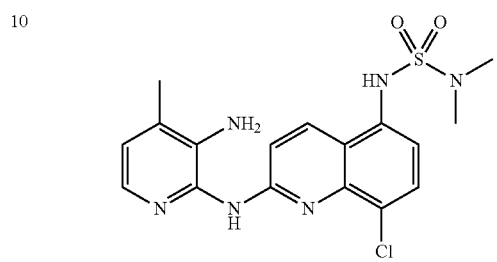 |
| 11 | 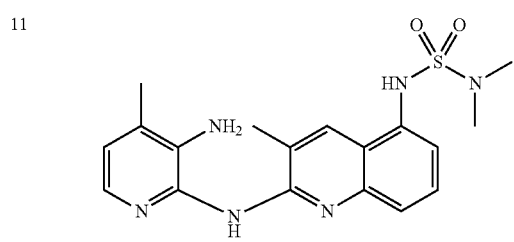 |
| 12 | 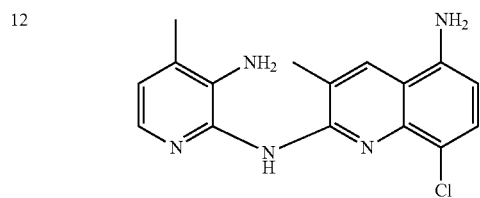 |
TABLE I-continued
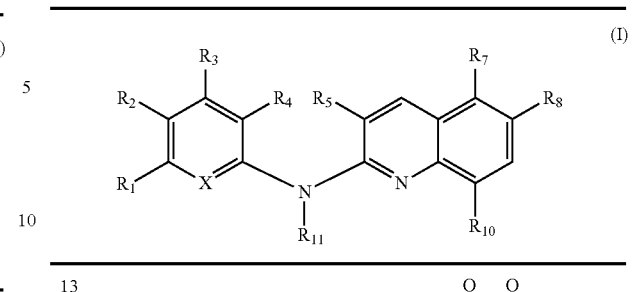
| 13 | 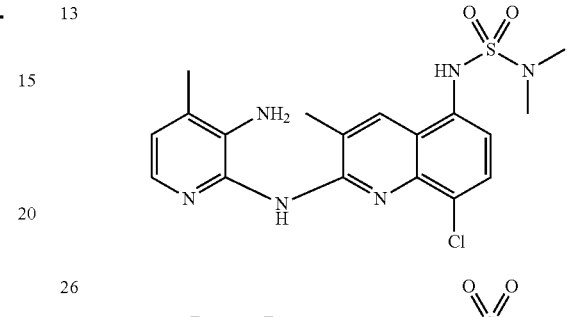 |
|---|---|
| 26 | 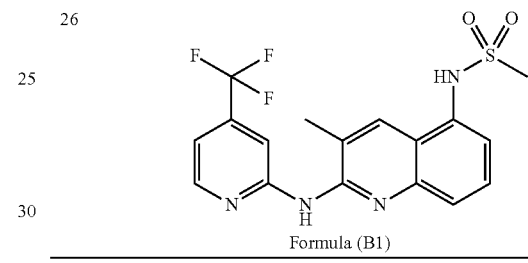<br>Formula (B1) |
| 14 | 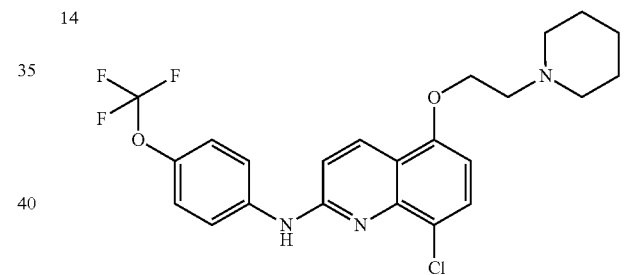 |
| 15 | 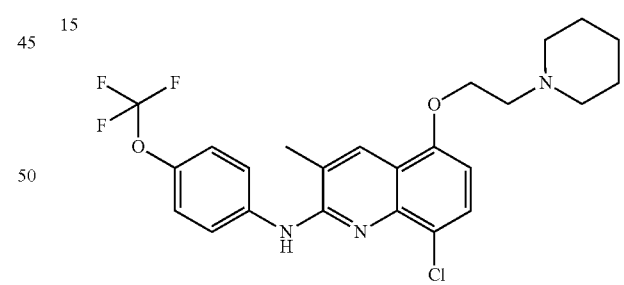 |
| 16 | 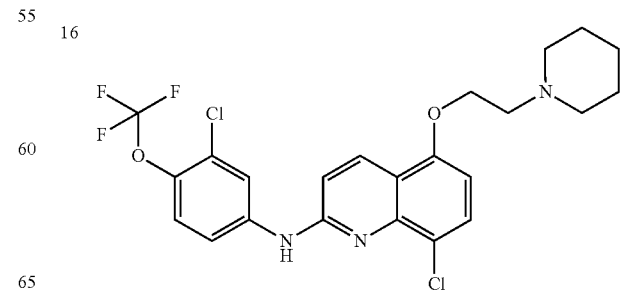 |

TABLE I-continued
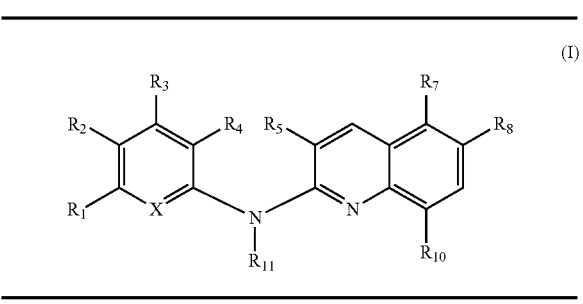
17 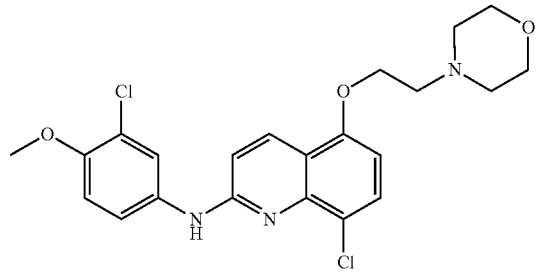 [SMILES: COc1ccc(Nc2ccc3c(OCCN4CCOCC4)ccc(Cl)c3n2)cc1Cl]
18 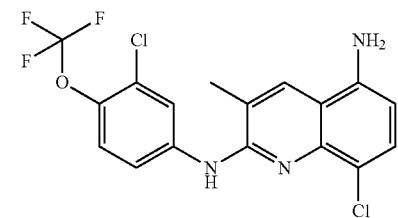 [SMILES: Cc1cc2c(N)ccc(Cl)c2nc1Nc1ccc(OC(F)(F)F)c(Cl)c1]
19 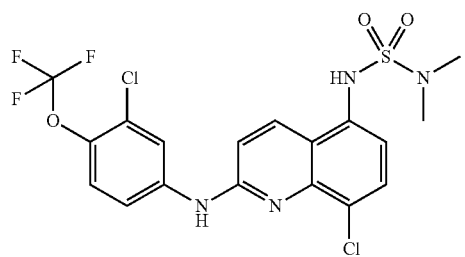 [SMILES: CN(C)S(=O)(=O)Nc1ccc(Cl)c2nc(Nc3ccc(OC(F)(F)F)c(Cl)c3)ccc12]
20 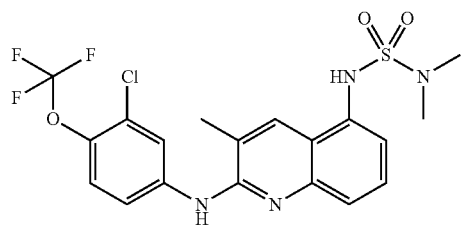 [SMILES: Cc1cc2c(NS(=O)(=O)N(C)C)cccc2nc1Nc1ccc(OC(F)(F)F)c(Cl)c1]
TABLE I-continued
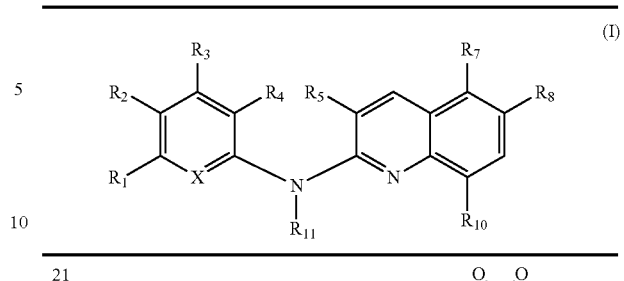
21 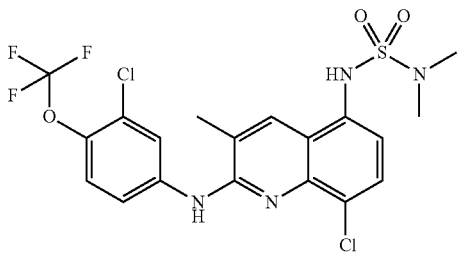 [SMILES: Cc1cc2c(NS(=O)(=O)N(C)C)ccc(Cl)c2nc1Nc1ccc(OC(F)(F)F)c(Cl)c1]
22 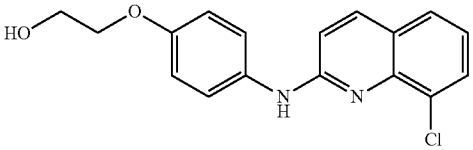 [SMILES: OCCOc1ccc(Nc2ccc3cccc(Cl)c3n2)cc1]
23 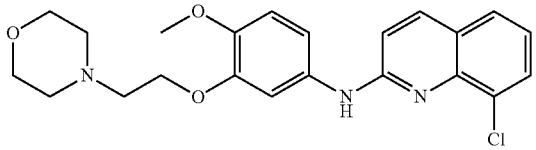 [SMILES: COc1ccc(Nc2ccc3cccc(Cl)c3n2)cc1OCCN1CCOCC1]
24 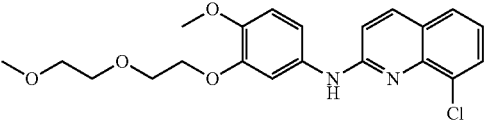 [SMILES: COCCOCCOc1cc(Nc2ccc3cccc(Cl)c3n2)ccc1OC]
25 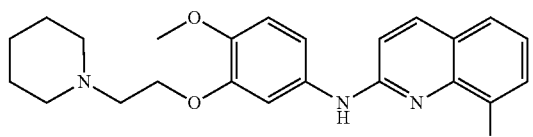
27 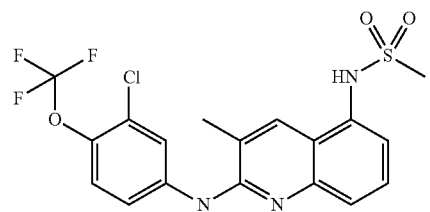
TABLE II
| Ex | Characterizations |
|---|---|
| 1 | $^1$H NMR (300 MHz, CDCl$_3$) δ 9.55 (s, 1H), 8.49-8.37 (m, 2H), 7.87 (s, 1H), 7.66 (d, J = 8.4, 1H), 7.18 (d, J = 4.7, 1H), 6.99 (d, J = 9.0, 1H), 6.67 (d, J = 8.4, 1H), 4.27 (t, J = 5.6, 2H), 3.81-3.69 (m, 4H), 2.93 (t, J = 5.7, 2H), 2.70-2.58 (m, 4H) $^{13}$C NMR (75 MHz, CDCl$_3$) δ 154.14, 153.54, 152.65, 148.80, 143.96, 140.86, |

TABLE II-continued

| Ex | Characterizations |
|---|---|
| | 133.52, 129.83, 123.39, 117.53, 112.69, 104.06, 67.19, 66.98, 57.75, 54.36 |
| | $[M + H]^+ = 453.2$ |
| 2 | $^1$H NMR (300 MHz, MeOD) δ 8.29 (d, J = 8.0, 1H), 7.58 (d, J = 5.4, 1H), 7.53 (d, J = 8.6, 1H), 7.27 (d, J = 9.7, 1H), 6.86 (d, J = 3.6, 1H), 6.69 (d, J = 9.0, 1H), 4.24 (s, 2H), 3.71 (s, 4H), 2.89 (s, 2H), 2.63 (s, 4H), 2.25 (s, 3H) |
| | $[M + H]^+ = 414.2$ |
| 3 | $^1$H NMR (300 MHz, CDCl$_3$) δ 9.56 (s, 1H), 8.44 (d, J = 6.2, 2H), 7.93 (s, 1H), 7.66 (d, J = 8.6, 1H), 7.18 (s, 1H), 6.98 (d, J = 8.5, 1H), 6.67 (d, J = 8.0, 1H), 4.27 (s, 2H), 2.92 (s, 2H), 2.59 (s, 4H), 1.64 (s, 5H), 1.48 (s, 2H) |
| | $^{13}$C NMR (75 MHz, CDCl$_3$) δ 153.5, 152.7, 148.5, 143.6, 133.3, 129.7, 123.0, 117.2, 113.0, 112.9, 112.4, 109.6, 103.7, 66.0, 57.6, 54.9, 25.7, 23.5 |
| | $[M + H]^+ = 451.1$ |
| 4 | $^1$H NMR (300 MHz, CDCl$_3$) δ 9.78 (s, 1H), 8.41 (d, J = 5.1, 1H), 8.23 (s, 1H), 7.84 (s, 1H), 7.59 (d, J = 8.4, 1H), 7.18 (d, J = 5.0, 1H), 6.65 (d, J = 8.4, 1H), 4.27 (t, J = 5.9, 2H), 2.94 (t, J = 5.8, 2H), 2.62 (s, 4H), 2.51 (s, 3H), 1.66 (s, 5H), 1.48 (s, 2H) |
| | $^{13}$C NMR (75 MHz, CDCl$_3$) δ 148.4, 132.2, 128.5, 113.3, 109.9, 103.7, 66.6, 57.6, 54.9, 25.7, 23.6, 17.3 |
| | $[M + H]^+ = 465.2$ |
| 5 | $[M + H]^+ = 426.2$ |
| 6 | $[M + H]^+ = 446.1$ |
| 7 | $[M + H]^+ = 426.1$ |
| 8 | $[M + H]^+ = 353.1$ |
| 9 | $[M + H]^+ = 460.1$ |
| 10 | $[M + H]^+ = 407.1$ |
| 11 | $[M + H]^+ = 387.2$ |
| 12 | $[M + H]^+ = 314.1$ |
| 13 | $[M + H]^+ = 421.2$ |
| 26 | $^1$H NMR (300 MHz, CDCl$_3$) δ 9.30 (s, 1H), 8.44 (d, J = 5.1, 1H), 8.20 (s, 1H), 7.87 (d, J = 8.1, 1H), 7.64 (s, 1H), 7.59 (t, J = 7.9, 1H), 7.41 (d, J = 7.9, 1H), 7.19 (d, J = 5.0, 1H), 6.51 (s, 1H), 3.08 (s, 3H), 2.54 (s, 3H) |
| | $[M + H]^+ = 397.2$ |
| 14 | $^1$H NMR (300 MHz, CDCl$_3$) δ 8.32 (d, J = 9.0, 1H), 7.90 (d, J = 8.9, 2H), 7.58 (d, J = 8.4, 1H), 7.23 (d, J = 8.5, 2H), 7.01 (s, 1H), 6.86 (d, J = 9.0, 1H), 6.59 (d, J = 8.5, 1H), 4.24 (t, J = 5.8, 2H), 2.90 (t, J = 5.8, 2H), 2.58 (s, 4H), 1.63 (s, 4H), 1.46 (s, 2H) |
| | $^{13}$C NMR (75 MHz, CDCl$_3$) δ153.4, 144.0, 138.6, 133.0, 129.5, 121.9, 120.3, 116.8, 111.4, 103.1, 66.6, 57.6, 54.9, 25.8, 23.6 |
| | $[M + H]^+ = 466.1$ |
| 15 | $^1$H NMR (300 MHz, CDCl$_3$) δ 8.20-8.11 (m, 3H), 7.53 (d, J = 8.4, 1H), 7.24 (d, J = 8.9, 2H), 6.75 (s, 1H), 6.59 (d, J = 8.4, 1H), 4.25 (s, 2H), 2.92 (s, 2H), 2.60 (s, 4H), 2.43 (s, 3H), 1.65 (s, 4H), 1.47 (s, 2H) |
| | $^{13}$C NMR (75 MHz, CDCl$_3$) δ 153.19, 152.81, 143.89, 143.15, 139.19, 131.96, 128.43, 122.75, 121.93, 120.09, 119.28, 117.33, 103.50, 67.40, 66.94, 58.06, 55.32, 26.20, 24.35, 17.75. |
| | $[M + H]^+ = 480.2$ |
| 16 | $^1$H NMR (300 MHz, CDCl$_3$) δ 8.47 (d, J = 2.0, 1H), 8.27 (d, J = 8.9, 1H), 7.66 (dd, J = 1.9, 9.1, 1H), 7.55 (d, J = 8.3, 1H), 7.23 (s, 1H), 7.14 (s, 1H), 6.79 (d, J = 8.8, 1H), 6.56 (d, J = 8.4, 1H), 4.22 (t, J = 5.7, 2H), 2.91 (t, J = 5.7, 2H), 2.59 (s, 4H), 1.64 (s, 4H), 1.46 (s, 2H). |
| | $[M + H]^+ = 500.0$ |
| 17 | $^1$H NMR (300 MHz, CDCl$_3$) δ 8.31 (d, J = 8.9, 1H), 7.95 (d, J = 2.8, 1H), 7.61 (t, J = 9.1, 2H), 6.97 (d, J = 8.9, 1H), 6.84 (d, J = 8.8, 1H), 6.59 (d, J = 8.5, 1H), 4.25 (t, J = 5.4, 2H), 3.92 (s, 3H), 3.79-3.72 (m, 1H), 2.92 (t, J = 5.5, 2H), 2.68-2.60 (m, 5H) |
| | $^{13}$C NMR (75 MHz, CDCl$_3$) δ 156.13, 154.04, 153.27. 143.58, 136.51, 132.15, 129.06, 123.71, 122.89, 118.50, 116.18, 104.15, 100.01, 67.00, 66.85, 57.54, 56.39, 54.17. |
| | $[M + H]^+ = 448.2$ |
| 18 | $[M + H]^+ = 402.1$ |
| 19 | $[M + H]^+ = 495.0$ |
| 20 | $[M + H]^+ = 475.1$ |
| 21 | $[M + H]^+ = 509.1$ |
| 22 | $^1$H NMR (300 MHz, CDCl$_3$) δ 7.99 (d, J = 8.8, 1H), 7.73 (dd, J = 1.2, 7.6, 1H), 7.63 (dd, J = 1.0, 8.0, 1H), 7.28 (dd, J = 4.8, 12.7, 1H), 7.01 (d, J = 8.8, 1H), 6.83 (d, J = 8.8, 2H), 6.64 (d, J = 8.8, 2H), 4.93-4.84 (m, 2H), 4.39-4.30 (m, 2H) |
| 23 | $^1$H NMR (300 MHz, CDCl$_3$) δ 8.06 (d, J = 1.9, 1H), 7.85 (d, J = 8.9, 1H), 7.70 (dd, J = 1.2, 7.6, 1H), 7.53 (dd, J = 1.0, 7.9, 1H), 7.18 (t, J = 7.8, 1H), 6.99 (s, 1H), 6.93 (dd, J = 2.4, 8.6, 1H), 6.85 (dd, J = 2.9, 8.8, 2H), 4.29 (t, J = 6.1, 2H), 3.85 (s, 3H), 3.78-3.68 (m, 4H), 2.88 (t, J = 6.1, 2H), 2.66-2.52 (m, 4H) |
| | $[M + H]^+ = 414.1$ |
| 24 | $^1$H NMR (300 MHz, CDCl$_3$) δ 7.86 (d, J = 8.9, 1H), 7.79 (d, J = 2.2, 1H), 7.69 (dd, J = 1.2, 7.6, 1H), 7.53 (dd, J = 1.1, 8.0, 1H), 7.18 (t, J = 7.8, 1H), 7.05 (td, J = 2.3, 8.8, 1H), 6.95 (s, 1H), 6.87 (d, J = 8.9, 2H), 4.30 (dd, J = 3.8, 9.0, 2H), 3.92 (t, J = 5.1, 2H), 3.85 (s, 2H), 3.72 (s, 2H), 3.60-3.55 (m, 2H), 3.38 (d, J = 1.8, 3H) |
| | $[M + H]^+ = 403.2$ |
| 25 | $^1$H NMR (300 MHz, CDCl$_3$) δ 7.88 (d, J = 8.9, 1H), 7.82 (d, J = 2.0, 1H), 7.70 (d, J = 7.6, 1H), 7.55 (d, J = 7.9, 1H), 7.19 (t, J = 7.8, 1H), 6.99 (dd, J = 2.3, 8.5, 1H), |

TABLE II-continued

| Ex | Characterizations |
|---|---|
| | 6.87 (d, J = 8.8, 2H), 6.84 (s, 1H), 4.27 (t, J = 6.4, 2H), 3.87 (s, 3H), 2.87 (t, J = 6.4, 2H), 2.54 (s, 4H), 1.61 (s, 4H), 1.45 (d, J = 5.2, 2H) [M + H]$^+$ = 412.1 |
| 27 | [M + H]$^+$ = 446.1 |

The following examples are provided as illustrations and in no way limit the scope of this invention.

The following examples illustrate in detail the preparation of some compounds according to the invention. The structures of the products obtained have been confirmed by NMR spectra.

EXAMPLES

Example 1

Compound (2) in Table I 4-chloro-3-nitrophenol (5 g, 28.8 mmol, 1 eq.) was placed in dimethylformamide (96 mL) with 4-(2-chloro-ethyl)morpholine (16 g, 86.4 mmol, 3 eq.), Cs$_2$CO$_3$ (65 g, 0.20 mmol, 7 eq.), KI (10.5 g, 63.4 mmol, 2.2 eq.). The reaction mixture was heated at 80° C. and stirred for 20 hours. The reaction mixture was then concentrated under reduced pressure and the resulting residue was diluted with ethyl acetate. The organic phase was washed with a 1% NaOH aqueous solution, dried over MgSO$_4$, filtered and concentrated under reduced pressure. The resulting residue was purified by column chromatography on silica gel to afford 4-(2-(4-chloro-3-nitrophenoxy)ethyl)morpholine. (7.5 g, 96%).

$^1$H NMR (300 MHz, CDCl$_3$) δ 7.43 (d, J=4.5, 1H), 7.41 (d, J=1.3, 1H), 7.08 (dd, J=2.9, 9.0, 1H), 4.14 (t, J=5.6, 2H), 3.78-3.68 (m, 4H), 2.82 (t, J=5.6, 2H), 2.62-2.51 (m, 4H).

4-(2-(4-chloro-3-nitrophenoxy)ethyl)morpholine. (7.5 g, 28.0 mmol, 1 eq.) and tin (II) chloride dihydrate (33 g, 146.9 mmol, 5 eq.) were placed in EtOH (280 mL), heated at 60° C. and stirred for 19 hours. The reaction mixture was then concentrated under reduced pressure and the resulting residue was diluted with ethyl acetate. The organic phase was washed with a 1N NaOH aqueous solution, dried over MgSO$_4$, filtered and concentrated under reduced pressure to afford 2-chloro-5-(2-morpholinoethoxy)aniline (5.8 g, 80%).

$^1$H NMR (300 MHz, CDCl$_3$) δ 7.10 (d, J=8.7, 1H), 6.31 (d, J=2.8, 1H), 6.25 (dd, J=2.8, 8.7, 1H), 4.02 (d, J=5.7, 2H), 3.76-3.68 (m, 4H), 2.76 (t, J=5.7, 2H), 2.59-2.50 (m, 4H).

2-chloro-5-(2-morpholinoethoxy)aniline (1.9 g, 7.4 mmol, 1 eq.) was placed in a mixture of acetone (2.5 mL) and water (3.2 mL) in the presence of K$_2$CO$_3$ (2.1 g, 14.4 mmol, 2 eq.). Cinnamoyl chloride (1.2 g, 7.4 mmol, 1 eq.) was then added at 0° C. The reaction mixture was allowed to warm-up to room temperature, stirred for 2 hours and extracted with ethyl acetate. The organic phase was dried over MgSO$_4$, filtered and concentrated under reduced pressure. The resulting residue was purified by column chromatography on silica gel to afford N-(2-chloro-5-(2-morpholinoethoxy)phenyl)cinnamamide (1.7 g, 60%).

$^1$H NMR (300 MHz, CDCl$_3$) δ 8.24 (d, J=2.7, 1H), 7.85 (s, 1H), 7.74 (d, J=15.5, 1H), 7.58-7.49 (m, 2H), 7.41-7.33 (m, 3H), 7.23 (d, J=8.9, 1H), 6.65-6.55 (m, 2H), 4.11 (t, J=5.5, 2H), 3.75-3.67 (m, 4H), 2.78 (t, J=5.6, 2H), 2.60-2.49 (m, 4H).

MS (ESI) [M+H]$^+$=387.3

N-(2-chloro-5-(2-morpholinoethoxy)phenyl)cinnamamide (800 mg, 2.1 mmol, 1 eq.) was placed in chlorobenzene (1.9 mL), in the presence of aluminium trichloride (1.6 g, 12.4 mmol, 6 eq.). The reaction mixture was heated at 125° C. and stirred for 2 hours. After cooling down to room temperature, it was diluted with a water and ice mixture and extracted with ethyl acetate. The organic phase was dried over MgSO$_4$, filtered and concentrated under reduced pressure. The resulting residue was purified by column chromatography on silica gel to afford 8-chloro-5-(2-morpholinoethoxy)quinolin-2 (1H)-one (220 mg, 34%).

$^1$H NMR (300 MHz, CDCl$_3$) δ 8.98 (s, 1H), 8.12 (d, J=9.8, 1H), 7.44 (d, J=8.8, 1H), 6.61 (t, J=10.0, 2H), 4.22 (t, J=5.6, 2H), 3.77-3.66 (m, 4H), 2.89 (t, J=5.7, 2H), 2.66-2.52 (m, 4H).

8-chloro-5-(2-morpholinoethoxy)quinolin-2(1H)-one (200 mg, 0.6 mmol, 1 eq.) was placed in acetonitrile (1.7 mL) in the presence of POCl$_3$ (301 μL, 3.2 mmol, 5 eq.) and triethylammonium chloride (738 mg, 3.2 mmol, 5 eq.). The reaction mixture was stirred at 120° C. for 3 hours. The mixture was then concentrated under reduced pressure and, after adding water to the residue (5 mL), was stirred at room temperature during 30 minutes. Then the resulting precipitate was washed with water and filtered to give 4-(2-((2,8-dichloroquinolin-5-yl)oxy)ethyl)morpholine (234 mg, 100%).

$^1$H NMR (300 MHz, d6-DMSO) δ 8.69 (d, J=8.8, 1H), 7.84 (d, J=7.4, 1H), 7.65 (d, J=8.8, 1H), 7.16 (s, 1H), 4.58 (s, 3H), 3.85 (s, 4H), 3.65 (s, 2H), 3.33 (s, 4H).

MS (ESI) [M+H]$^+$=327.1

A reaction mixture of 4-(2-((2,8-dichloroquinolin-5-yl) oxy)ethyl)morpholine (81.5 mg, 0.25 mmol, 1 eq.), 2-amino-3-nitropyridine (41.3 mg, 0.27 mmol, 1.1 eq.), Pd(OAc)$_2$ (1.1 mg, 2 mol %), XantPhos (2.9 mg, 2 mol %) and Cs$_2$CO$_3$ (228 mg, 2.8 eq.)) in t-BuOH (1 mL) was heated at 90° C. and stirred for 20 hours. The reaction mixture was then concentrated under reduced pressure and the resulting residue was diluted with ethyl acetate. The organic phase was washed with water, dried over MgSO$_4$, filtered and concentrated under reduced pressure. The resulting residue was purified by column chromatography on silica gel to afford 8-chloro-N-(4-methyl-3-nitropyridin-2-yl)-5-(2-morpholinoethoxy) quinolin-2-amine (41 mg, 37%).

$^1$H NMR (300 MHz, CDCl$_3$) δ 8.42 (dd, J=9.1, 42.5, 1H), 8.27 (d, J=5.1, 1H), 7.97 (d, J=9.6, OH), 7.50 (dd, J=8.5, 60.4, 1H), 6.81 (dd, J=7.7, 14.6, 1H), 6.60 (dd, J=8.4, 22.9, 1H), 4.31-4.14 (m, 2H), 3.80-3.67 (m, 4H), 2.96-2.83 (m, 2H), 2.62 (s, 4H), 2.42 (d, J=62.1, 3H).

MS (ESI) [M+H]=444.2

8-chloro-N-(4-methyl-3-nitropyridin-2-yl)-5-(2-morpholinoethoxy)quinolin-2-amine (35 mg, 79 μmol, 1 eq.) and tin (II) chloride dihydrate (89 mg, 394 μmol, 5 eq.) were placed in ethanol (79 μL), heated at 60° C. and stirred for 19 hours. The reaction mixture was then concentrated under reduced pressure and the resulting residue was diluted with ethyl acetate. The organic phase was washed with a 1N NaOH aqueous solution, dried over MgSO$_4$, filtered and concentrated under reduced pressure. The resulting residue was purified by column chromatography on silica gel to afford compound (2) (33 mg, 100%).

$^1$H NMR (300 MHz, MeOD) δ 8.29 (d, J=8.0, 1H), 7.58 (d, J=5.4, 1H), 7.53 (d, J=8.6, 1H), 7.27 (d, J=9.7, 1H), 6.86 (d, J=3.6, 1H), 6.69 (d, J=9.0, 1H), 4.24 (s, 2H), 3.71 (s, 4H), 2.89 (s, 2H), 2.63 (s, 4H), 2.25 (s, 3H)

MS (ESI) [M+H]$^+$=414.2

Example 2

Compound (4) in Table I 4-chloro-3-nitrophenol (2.5 g, 14.4 mmol, 1 eq.) was placed in dimethylformamide (48 mL) with 4-(2-chloroethyl)piperidine (8 g, 43.2 mmol, 3 eq.), Cs$_2$CO$_3$ (33 g, 100.8 mmol, 7 eq.), KI (5.3 g, 31.7 mmol, 2.2 eq.). The reaction mixture was heated at 80° C. and stirred for 20 hours. The reaction mixture was then concentrated under reduced pressure and the resulting residue was diluted with ethyl acetate. The organic phase was washed with a 1% NaOH aqueous solution, dried over MgSO$_4$, filtered and concentrated under reduced pressure. The resulting residue was purified by column chromatography on silica gel to afford 4-(2-(4-chloro-3-nitrophenoxy)ethyl)piperidine (2.3 g, 56%).

$^1$H NMR (300 MHz, CDCl$_3$) δ 7.38 (s, 1H), 7.36 (d, J=6.5, 1H), 7.04 (dd, J=3.0, 8.9, 1H), 4.08 (t, J=5.9, 2H), 2.73 (t, J=5.9, 2H), 2.50-2.39 (m, 4H), 1.62-1.50 (m, 4H), 1.41 (dd, J=5.8, 11.0, 2H).

4-(2-(4-chloro-3-nitrophenoxy)ethyl)piperidine (2.3 g, 8.1 mmol, 1 eq.) and tin (II) chloride dihydrate (9.1 g, 40.4 mmol, 5 eq.) were placed in EtOH (81 mL). The reaction mixture was heated at 60° C. and stirred for 19 hours. The reaction mixture was then concentrated under reduced pressure and the resulting residue was diluted with ethyl acetate. The organic phase was washed with a 1N NaOH aqueous solution, dried over MgSO$_4$, filtered and concentrated under reduced pressure to afford 2-chloro-5-(2-piperidinoethoxy)aniline (1.9 g, 92%).

$^1$H NMR (300 MHz, CDCl$_3$) δ 7.09 (d, J=8.7, 1H), 6.32 (d, J=2.7, 1H), 6.26 (dd, J=2.8, 8.7, 1H), 4.00 (s, 2H), 2.73 (t, J=6.1, 2H), 2.47 (d, J=4.9, 4H), 1.60 (dd, J=5.6, 11.1, 4H), 1.44 (d, J=5.1, 2H).

2-chloro-5-(2-piperidinoethoxy)aniline (705 mg, 3.9 mmol, 1 eq.) was placed in a mixture of acetone (653 µL) and water (852 µL) in the presence of K$_2$CO$_3$ (1.1 g, 7.8 mmol, 2 eq.). (E)-2-methyl-3-phenylacryloyl chloride (705 mg, 3.9 mmol, 1 eq.) was then added at 0° C. The reaction mixture was allowed to warm-up to room temperature, stirred for 2 hours and extracted with ethyl acetate. The organic phase was dried over MgSO$_4$, filtered and concentrated under reduced pressure. The resulting residue was purified by column chromatography on silica gel to afford (E)-N-(2-chloro-5-(2-(piperidin-1-yl)ethoxy)phenyl)-2-methyl-3-phenylacrylamide (500 mg, 66%).

$^1$H NMR (300 MHz, CDCl$_3$) δ 8.22 (d, J=2.6, 1H), 8.18 (s, 1H), 7.51 (s, 1H), 7.36 (s, 4H), 7.33-7.26 (m, 1H), 7.21 (d, J=8.8, 1H), 6.61 (d, J=8.8, 1H), 4.09 (t, J=5.9, 2H), 2.74 (t, J=5.9, 2H), 2.47 (s, 4H), 2.21 (s, 3H), 1.57 (d, J=5.1, 4H), 1.41 (s, 2H).

MS (ESI) [M+H]$^+$=399.2

(E)-N-(2-chloro-5-(2-(piperidin-1-yl)ethoxy)phenyl)-2-methyl-3-phenylacrylamide (100 mg, 0.2 mmol, 1 eq.) was placed in chlorobenzene (500 µL), in the presence of aluminium trichloride (201 mg, 1.5 mmol, 6 eq.). The reaction mixture was heated at 125° C. and stirred for 2 hours. After cooling down to room temperature, it was diluted with a water and ice mixture and extracted with ethyl acetate. The organic phase was dried over MgSO$_4$, filtered and concentrated under reduced pressure. The resulting residue was purified by column chromatography on silica gel to afford 8-chloro-3-methyl-5-(2-(piperidin-1-yl)ethoxy)quinolin-2(1H)-one (25 mg, 31%).

$^1$H NMR (300 MHz, CDCl$_3$) δ 7.96 (s, 1H), 7.36 (d, J=8.6, 1H), 6.58 (d, J=8.8, 1H), 4.24 (s, 2H), 2.94 (s, 2H), 2.63 (s, 4H), 2.15 (s, 3H), 1.66 (s, 4H), 1.52-1.44 (m, 2H).

8-chloro-3-methyl-5-(2-(piperidin-1-yl)ethoxy)quinolin-2(1H)-one (160 mg, 0.5 mmol, 1 eq.) was placed in acetonitrile (1.2 mL) in the presence of POCl$_3$ (233 µL, 2.5 mmol, 5 eq.) and triethylammonium chloride (570 mg, 2.5 mmol, 5 eq.). The reaction mixture was stirred at 120° C. during 3 hours. The mixture was then concentrated under reduced pressure and, after adding water to the residue (5 mL), was stirred at room temperature during 30 minutes. Then the resulting precipitate was washed with water and filtered to give 2,8-dichloro-3-methyl-5-(2-(piperidin-1-yl)ethoxy)quinoline (170 mg, 100%).

$^1$H NMR (300 MHz, d6-DMSO) δ 10.60-10.31 (m, 1H), 8.81 (s, 1H), 7.86 (d, J=8.5, 1H), 7.14 (s, 1H), 4.56 (s, 2H), 3.59 (s, 4H), 3.04 (s, 2H), 2.54 (s, 3H), 1.81 (s, 5H).

A reaction mixture of 2,8-dichloro-5-(2-(piperidin-1-yl)ethoxy)quinoline (55 mg, 162 µmol, 1 eq.), 2-amino-4-trifluoromethylpyridine (29 mg, 178 µmol, 1.1 eq.), Pd(OAc)$_2$ (1 mg, 2 mol %), XantPhos (2 mg, 2 mol %) and Cs$_2$CO$_3$ (148 mg, 2.8 eq.) in t-BuOH (650 µL) was heated at 90° C. and stirred for 20 hours. The reaction mixture was then concentrated under reduced pressure and the resulting residue was diluted with ethyl acetate. The organic phase was washed with water, dried over MgSO$_4$, filtered and concentrated under reduced pressure. The resulting residue was purified by column chromatography on silica gel to afford compound (4) (50 mg, 66%).

$^1$H NMR (300 MHz, CDCl$_3$) δ 9.78 (s, 1H), 8.41 (d, J=5.1, 1H), 8.23 (s, 1H), 7.84 (s, 1H), 7.59 (d, J=8.4, 1H), 7.18 (d, J=5.0, 1H), 6.65 (d, J=8.4, 1H), 4.27 (t, J=5.9, 2H), 2.94 (t, J=5.8, 2H), 2.62 (s, 4H), 2.51 (s, 3H), 1.66 (s, 5H), 1.48 (s, 2H)

$^{13}$C NMR (75 MHz, CDCl$_3$) δ 148.4, 132.2, 128.5, 113.3, 109.9, 103.7, 66.6, 57.6, 54.9, 25.7, 23.6, 17.3

MS (ESI) [M+H]$^+$=465.2

Example 3

Compound (14) in Table I 4-chloro-3-nitrophenol (2.5 g, 14.4 mmol, 1 eq.) was placed in dimethylformamide (48 mL) with 4-(2-chloroethyl)piperidine (8 g, 43.2 mmol, 3 eq.), Cs$_2$CO$_3$ (33 g, 100.8 mmol, 7 eq.), KI (5.3 g, 31.7 mmol, 2.2 eq.). The reaction mixture was heated at 80° C. and stirred for 20 hours. The reaction mixture was then concentrated under reduced pressure and the resulting residue was diluted with ethyl acetate. The organic phase was washed with a 1% NaOH aqueous solution, dried over MgSO$_4$, filtered and concentrated under reduced pressure. The resulting residue was purified by column chromatography on silica gel to afford 4-(2-(4-chloro-3-nitrophenoxy)ethyl)piperidine (2.3 g, 56%).

$^1$H NMR (300 MHz, CDCl$_3$) δ 7.38 (s, 1H), 7.36 (d, J=6.5, 1H), 7.04 (dd, J=3.0, 8.9, 1H), 4.08 (t, J=5.9, 2H), 2.73 (t, J=5.9, 2H), 2.50-2.39 (m, 4H), 1.62-1.50 (m, 4H), 1.41 (dd, J=5.8, 11.0, 2H).

4-(2-(4-chloro-3-nitrophenoxy)ethyl)piperidine (2.3 g, 8.1 mmol, 1 eq.) and tin (II) chloride dihydrate (9.1 g, 40.4 mmol, 5 eq.) were placed in EtOH (81 mL). The reaction mixture was heated at 60° C. and stirred for 19 hours. The reaction mixture was then concentrated under reduced pressure and the resulting residue was diluted with ethyl acetate. The organic phase was washed with a 1N NaOH aqueous solution, dried over MgSO$_4$, filtered and concentrated under reduced pressure. The resulting residue was purified by column chromatography on silica gel to afford 2-chloro-5-(2-piperidinoethoxy)aniline (1.9 g, 92%).

$^1$H NMR (300 MHz, CDCl$_3$) δ 7.09 (d, J=8.7, 1H), 6.32 (d, J=2.7, 1H), 6.26 (dd, J=2.8, 8.7, 1H), 4.00 (s, 2H), 2.73 (t, J=6.1, 2H), 2.47 (d, J=4.9, 4H), 1.60 (dd, J=5.6, 11.1, 4H), 1.44 (d, J=5.1, 2H)

2-chloro-5-(2-piperidinoethoxy)aniline (500 mg, 1.9 mmol, 1 eq.) was placed in mixture of acetone (653 µL) and water (852 µL) in the presence of K$_2$CO$_3$ (541 m g, 3.9 mmol, 2 eq.). Cinnamoyl chloride (326 mg, 1.9 mmol, 1 eq.) was then added at 0° C. The reaction mixture was allowed to warm-up to room temperature, stirred for 2 hours and extracted with ethyl acetate. The organic phase was dried over MgSO$_4$, filtered and concentrated under reduced pressure. The resulting residue was purified by column chromatography on silica gel to afford N-(2-chloro-5-(2-(piperidin-1-yl)ethoxy)phenyl)cinnamamide (521 mg, 69%).

$^1$H NMR (300 MHz, CDCl$_3$) δ 8.23 (s, 1H), 7.83 (s, 1N), 7.75 (d, J=15.5, 1H), 7.53 (d, J=3.8, 2H), 7.40-7.32 (m, 3H), 7.22 (d, J=8.9, 1H), 6.65-6.53 (m, 2H), 4.10 (t, J=5.9, 2H), 2.75 (t, J=5.9, 2H), 2.48 (s, 4H), 1.65-1.52 (m, 4H), 1.43 (d, J=5.2, 2H)

N-(2-chloro-5-(2-(piperidin-1-yl)ethoxy)phenyl)cinnamamide (436 mg, 1.1 mmol, 1 eq.) was placed in chlorobenzene (2.1 mL), in the presence of aluminium trichloride (906 mg, 1.5 mmol, 6 eq.). The reaction mixture was heated at 125° C. and stirred for 2 hours. After cooling down to room temperature, it was diluted with a water and ice mixture and extracted with ethyl acetate. The organic phase was dried over MgSO$_4$, filtered and concentrated under reduced pressure. The resulting residue was purified by column chromatography on silica gel to afford 8-chloro-5-(2-(piperidin-1-yl)ethoxy)quinolin-2(1H)-one (225 mg, 67%).

$^1$H NMR (300 MHz, CDCl$_3$) δ 9.20 (s, 1H), 8.04 (d, J=9.6, 1H), 7.33 (d, J=8.3, 1H), 6.51 (t, J=8.4, 2H), 4.12 (s, 2H), 2.78 (s, 2H), 2.46 (s, 4H), 1.54 (s, 4H), 1.39 (s, 2H)

8-chloro-5-(2-(piperidin-1-yl)ethoxy)quinolin-2(1H)-one (275 mg, 0.9 mmol, 1 eq.) was placed in acetonitrile (2.3 mL) in the presence of POCl$_3$ (418 µL, 4.5 mmol, 5 eq.) and triethylammonium chloride (1 g, 4.5 mmol, 5 eq.). The reaction mixture was stirred at 120° C. during 3 hours. The mixture was then concentrated under reduced pressure and, after adding water to the residue (5 mL), was stirred at room temperature during 30 minutes. Then the resulting precipitate was washed with water and filtered to give 2,8-dichloro-5-(2-(piperidin-1-yl)ethoxy)quinoline (228 mg, 100%).

$^1$H NMR (300 MHz, d6-DMSO) δ 8.86 (d, J=8.7, 1H), 7.93 (s, 1H), 7.70 (d, J=8.6, 1H), 7.16 (s, 1H), 4.61 (s, 2H), 3.60 (s, 4H), 3.04 (s, 2H), 1.80 (s, 4H), 1.74-1.58 (m, 2H)

A reaction mixture of 2,8-dichloro-5-(2-(piperidin-1-yl)ethoxy)quinoline (75 mg, 231 µmol, 1 eq.), 4-(trifluoromethoxy)aniline (34 µL, 178 µmol, 1.1 eq.), Pd(OAc)$_2$ (1 mg, 2 mol %), XantPhos (3 mg, 2 mol %) and Cs$_2$CO$_3$ (210 mg, 2.8 eq.) in t-BuOH (924 µL) was heated at 90° C. and stirred for 20 hours. The reaction mixture was then concentrated under reduced pressure and the resulting residue was diluted with ethyl acetate. The organic phase was washed with water, dried over MgSO$_4$, filtered and concentrated under reduced pressure. The resulting residue was purified by column chromatography on silica gel to give 8-chloro-5-(2-(piperidin-1-yl)ethoxy)-N-(4-(trifluoromethyl)pyridin-2-yl)quinolin-2-amine (14) (63 mg, 59%).

$^1$H NMR (300 MHz, CDCl$_3$) δ 8.32 (d, J=9.0, 1H), 7.90 (d, J=8.9, 2H), 7.58 (d, J=8.4, 1H), 7.23 (d, J=8.5, 2H), 7.01 (s, 1H), 6.86 (d, J=9.0, 1H), 6.59 (d, J=8.5, 1H), 4.24 (t, J=5.8, 2H), 2.90 (t, J=5.8, 2H), 2.58 (s, 4H), 1.63 (s, 4H), 1.46 (s, 2H)

$^{13}$C NMR (75 MHz, CDCl$_3$) δ153.4, 144.0, 138.6, 133.0, 129.5, 121.9, 120.3, 116.8, 111.4, 103.1, 66.6, 57.6, 54.9, 25.8, 23.6

MS (ESI) [M+H]$^+$=466.1

Example 4

Compound (23) in Table I 2-methoxy-5-nitrophenol (254 mg, 1.5 mmol, 1 eq.) was placed in dimethylformamide (3 mL) with 4-(2-chloro-ethyl)morpholine hydrochloride (837 mg, 4.5 mmol, 3 eq.), Cs$_2$CO$_3$ (3.4 g, 10.7 mmol, 7 eq.), KI (547 mg, 3.3 mmol, 2.2 eq.). The reaction mixture was heated at 80° C. and stirred for 20 hours. The reaction mixture was then concentrated under reduced pressure and the resulting residue was diluted with ethyl acetate. The organic phase was washed with a 1% NaOH aqueous solution, dried over MgSO$_4$, filtered and concentrated under reduced pressure. The resulting residue was purified by column chromatography on silica gel to afford 4-(2-(2-methoxy-5-nitrophenoxy)ethyl)morpholine (386 mg, 91%).

$^1$H NMR (300 MHz, MeOD) δ 7.92 (dd, J=2.6, 9.0, 1H), 7.82 (d, J=2.6, 1H), 7.10 (d, J=9.0, 1H), 4.23 (t, J=5.4, 2H), 3.94 (s, 3H), 3.76-3.67 (m, 4H), 2.85 (t, J=5.4, 2H), 2.67-2.59 (m, 4H)

4-(2-(2-methoxy-5-nitrophenoxy)ethyl)morpholine (350 mg, 1.2 mmol, 1 eq.) and tin (II) chloride dihydrate (1.4 g, 6.20 mmol, 5 eq.) were placed in EtOH (12.3 mL). The reaction mixture was heated at 60° C. and stirred for 19 hours. The reaction mixture was then concentrated under reduced pressure and the resulting residue was diluted with ethyl acetate. The organic phase was washed with a 1N NaOH aqueous solution, dried over MgSO$_4$, filtered and concentrated under reduced pressure. The resulting residue was purified by column chromatography on silica gel to afford 4-methoxy-3-(2-morpholinoethoxy)aniline (143 mg, 46%).

$^1$H NMR (300 MHz, MeOD) δ 6.73 (d, J=8.5, 1H), 6.43 (d, J=2.5, 1H), 6.29 (dd, J=2.5, 8.4, 1H), 4.06 (t, J=5.6, 2H), 3.71 (s, 3H), 3.70-3.67 (m, 4H), 2.75 (t, J=5.6, 2H), 2.59-2.55 (m, 4H)

A reaction mixture of 2,8-dichloroquinoline (101 mg, 0.5 mmol, 1 eq.) and 4-methoxy-3-(2-morpholinoethoxy)aniline (143 mg, 0.55 mmol, 1.1 eq.), Pd(OAc)$_2$ (2.3 mg, 2 mol %), XantPhos (6 mg, 2 mol %) and Cs$_2$CO$_3$ (465 mg, 2.8 eq.)) in t-BuOH (2 mL) was heated at 90° C. and stirred for 20 hours. The reaction mixture was then concentrated under reduced pressure and the resulting residue was diluted with ethyl acetate. The organic phase was washed with water, dried over MgSO$_4$, filtered and concentrated under reduced pressure. The resulting residue was purified by column chromatography on silica gel to give compound (23) (44 mg, 21%).

$^1$H NMR (300 MHz, CDCl$_3$) δ 8.06 (d, J=1.9, 1H), 7.85 (d, J=8.9, 1H), 7.70 (dd, J=1.2, 7.6, 1H), 7.53 (dd, J=1.0, 7.9, 1H), 7.18 (t, J=7.8, 1H), 6.99 (s, 1H), 6.93 (dd, J=2.4, 8.6, 1H), 6.85 (dd, J=2.9, 8.8, 2H), 4.29 (t, J=6.1, 2H), 3.85 (s, 3H), 3.78-3.68 (m, 4H), 2.88 (t, J=6.1, 2H), 2.66-2.52 (m, 4H)

MS (ESI) [M+H]+=414.1

Pharmalogical Data

The compounds of the invention have been the subject of pharmacological tests which have demonstrated their relevance as active substances in therapy and in particular for preventing, inhibiting or treating AIDS.

Example 5

Development of IDC16 Derivative Compounds

The inventors have shown that compound IDC16 (BAKK-OUR et al., cited above, 2007) interacts functionally with the SF2/ASF complex and thus contributes to blocking alternative splicing during HIV replication, leading to the termination of the production of Tat protein.

Accordingly, the family of polycyclic indoles, to which compound IDC16 belongs, is known to exhibit the properties of DNA intercalating agents. Such compounds thus present a risk in terms of undesirable side effects.

The inventors thus sought to develop novel molecules exhibiting activity comparable to IDC16, in terms of activity inhibiting HIV splicing, but while not exhibiting the characteristics of DNA intercalating agents.

In their initial hypothesis, the inventors considered that the two polar heterocycles at the two ends of compound IDC16 were associated with its activity and that the two median rings were of less importance.

Based on this hypothesis, the inventors considered that:
the nitrogen of the indoline and of the D ring of IDC16 might act as acceptors of hydrogen bonds;
the N-methylated 4-pyridinone motif might be preserved in the analogues;
the flat tetracyclic geometry was not optimal and it might be wise to replace the B and C rings by other motifs to limit DNA intercalating properties.

Example 6

Inhibition of HIV-1 Production in Infected Peripheral Blood Mononuclear Cells (PBMCs)

Material and Methods

The first determination is that of the concentration of compound that exhibits the fewest side effects in terms of cell viability and progression of the cell cycle.

Within this framework, the peripheral blood mononuclear cells (PBMCs) of healthy donors are isolated by centrifugation on a FICOLL gradient. The cells are then activated two days to a density of $1.5 \times 10^6$ cells/ml in RPMI plutamax medium supplemented with 10% fetal calf serum (FCS), 40 U/ml of IL2 and 5 µg/ml PHA, in an incubator at 37° C., 5% $CO_2$.

A standard experiment using 96 plates to test 30 molecules in triplicates including positive and negative controls, is performed as follows:

PHA/IL2 activated PBMCs are washed with RPMI 10% FCS and resuspended at $1.5 \times 10^6$ cells/ml in RPMI glutamax 10% FCS, 40 U/ml 112. The cells are seeded in 96 wells (1.5 $10^5$ cells/well/100l). Viral infection is performed with 1 ng of AdaM/well. 100 µl of tested molecules at concentration of 20 µM are added to each well (10 µM final concentration). Virus production is determined by p24 antigen immunosorbent assays after 3 and 6 days of infection (Kit Innogenetics). Typically PBMCs are prepared from several healthy donors (around 11 different donors). Dose response curves were then established with selected compounds to determine $IC_{50}$.

Protocol for Cytotoxicity:

To evaluate the cytotoxicity of different compounds we used the same protocol as above to seed the HOS-CD4$^+$-CCR5$^+$ cells or PBMCs in a final volume of 50 µl, without adding the virus, and 50 µl of tested molecules. After an incubation for 6 days at 37° C., 20 µl of CellTiter96 AqueousOne solution is added to determine the number of viable cells in proliferation and cytotoxicity assays (Promega). CellTiter96 AqueousOne is a colorimetric assay solution that has many advantages compared to MTT assays and gives us satisfactory results.

We have also evaluated the effect of selected molecules on CD4 and CD8 proliferation using the division tracking dye carboxyfluorescein diacetate succinimidyl ester (CFSE) (In vitrogen).

Results:

The efficacy of compounds of the present invention is measured by the HIV-specific enzyme-linked immunosorbent assay, p24 ELISA. Drug efficacy is expressed as percent inhibition of the HIV p24 antigen in this rapid and sensitive assay. It is expected that compounds of the present invention exhibit an $IC_{50}$ of less than 100 µM in vitro when PBMCs from different donors were challenged with adaM HIV-1 strain. In accordance with particular embodiments, $IC_{50}$ are expected to be less than 10 µM, or even less than 1 nanomolar to picomolar amounts in vitro.

Among the tested compounds, the following results may be reported:

| Number of the tested compound | Activity |
| --- | --- |
| 1 | + |
| Chloride salt of 1 | ++ |
| 2 | + |
| Chloride salt of 2 | ++ |
| 17 | ++ |
| Chloride salt of 17 | ++ |
| 4 | ++ |
| Chloride salt of 4 | ++ |

As examples of pharmaceutically acceptable supports, the composition can include emulsions, microemulsions, oil in water emulsions, anhydrous lipids and water in oil emulsions or other types of emulsions.

The inventive composition can further include one or more additives such as diluents, excipients, stabilizers and preservatives. Such additives are well known to those skilled in the art and are described notably in "*Ullmann's Encyclopedia of Industrial Chemistry*, 6$^{th}$ Ed." (various editors, 1989-1998, Marcel Dekker) and in "*Pharmaceutical Dosage Forms and Drug Delivery Systems*" (ANSEL et al., 1994, WILLIAMS & WILKINS).

The aforementioned excipients are selected according to the dosage form and the desired mode of administration.

In this context they can be present in any pharmaceutical form which is suitable for enteral or parenteral administration, in association with appropriate excipients, for example in the form of plain or coated tablets, hard gelatine, soft shell capsules and other capsules, suppositories, or drinkable, such as suspensions, syrups, or injectable solutions or suspensions, in doses which enable the daily administration of from 0.1 to 1000 mg of active substance.

Still a further object consists of the use of at least one compound of formulae (I), (A1), (A1'), (B1) and (B1') as defined above, and compounds (1) to (27) and (i), (ii), (iii), (iv), (v), (vi), (vii) or (viii) as defined above, or one of its pharmaceutically acceptable salts according to the present invention in preparing a drug to treat, in a subject, a disease resulting from at least one splicing anomaly.

As used in the present application, the term "subject" refers to a mammal such as a rodent, cat, dog, primate or human, preferably said subject is a human.

Preferably, the inventive compounds have the ability to inhibit pre-messenger RNA splicing processes that are either constitutive or, more specifically, dependent on regulating sequences known as an ESE (exonic splicing enhancer), ISE (intronic splicing enhancer), ESS (exonic splicing silencer) and ISS (intronic splicing silencer).

In a particularly preferred way, splicing processes are either constitutive and/or or dependent on ESE regulating sequences.

Preferably, the present invention relates to the use of the at least one compound of formulae (I), (A1), (A1'), (B1) and (B1') as defined above and compounds (1) to (27) and (i), (ii), (iii), (iv), (v), (vi), (vii) or (viii) as defined above, or one of its pharmaceutically acceptable salts according to the present invention, for preparing a drug to treat, in a subject, AIDS.

Therefore, the present invention relates to one compound of formulae (I), (A1), (A1'), (B1) and (B1') as defined above and compound (1) to (27) and (i), (ii), (iii), (iv), (v), (vi), (vii) or (viii) or one of its acceptable salts as an agent for inhibiting, preventing or treating AIDS.

Another object of the invention relates to a therapeutic method for treating a subject for a genetic disease resulting from splicing anomalies comprising the administration of a therapeutically effective quantity of a compound of formulae (I), (A1), (A1'), (B1) and (B1'), compounds (1) to (27) and (i), (ii), (iii), (iv), (v), (vi), (vii) or (viii), as defined above, or one of its acceptable salts.

Preferably, said genetic disease resulting from splicing anomalies is AIDS.

A "therapeutically effective quantity" means a quantity that induces inhibition of the splicing of the pre-mRNAs of interest. Those skilled in the art will be able to determine said therapeutically effective quantity based on their general knowledge and on the methods described in the examples.

The compounds can be administered by any mode of administration such as, for example, by intramuscular, intravenous or oral route, etc.

Compounds of the present invention may, in appropriate cases be administered as prodrugs, such as esters, of compounds with which the invention is concerned. "Prodrug" means a compound which is convertible in vivo by metabolic means (e.g. by hydrolysis, reduction or oxidation) to a compound of the present invention. For example, an ester prodrug of a compound of the present invention may be convertible by hydrolysis in vivo to the parent molecule. Suitable esters of compounds of the present invention are for example acetates, citrates, lactates, tartrates, malonates, oxalates, salicylates, propionates, succinates, fumarates, maleates, methylene-bis-3-hydroxynaphthoates, gentisates, isethionates, di-p-toluoyltatrates, methanesulphonates, ethanesulphonates, benzenesulphonates, p-toluenesulphonates, cyclohexylsulfamates and quinates. Examples of ester prodrugs are those described by F. J. Leinweber, Drug Metab. Res., 1987, 18, 379. As used herein, references to the compounds of the present invention are meant to also include the prodrug forms.

In one embodiment according to the invention, said composition further includes an excipient making it possible to formulate the inventive compounds in such a way that said composition is provided in solid or liquid form to be prepared and administered by intravenous route.

The inventive compounds preferably will be administered by intravenous route at a concentration of 80-100 mg/m². The concentration will be chosen by those skilled in the art according to the organ or tissue to be treated, the state of advancement of the disease and the targeting mode used.

The invention claimed is:

1. A method of inhibiting replication of HIV-1 in a patient infected with HIV-1, comprising:
administrating to the patient an effective quantity of a compound of formula (I) or a pharmaceutically acceptable salt thereof to inhibit replication of HIV-1:

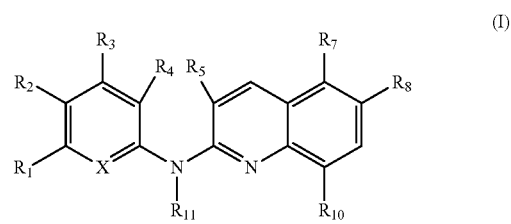

wherein:
X is $CR_0$ or N, i.e. forms together with the ring to which it belongs respectively a benzene or a pyridine group,
$R_0$, $R_1$, $R_2$, $R_3$, $R_4$, $R_7$, and $R_8$ independently represent:
a hydrogen atom,
a halogen atom, or
a group selected from:
a ($C_1$-$C_5$)alkyl group,
a ($C_3$-$C_6$)cycloalkyl group,
a ($C_1$-$C_5$)fluoroalkyl group,
a ($C_1$-$C_5$)alkoxy group,
a ($C_1$-$C_5$)fluoroalkoxy group,
a —CN group,
a —COOR$_a$ group,
a —NO$_2$ group,
a —NR$_a$R$_b$ group,
a —NR$_a$—SO$_2$—NR$_a$R$_b$ group,
a —NR$_a$—SO$_2$—R$_a$ group,
a —NR$_a$—C(=O)—R$_a$ group,
a —NR$_a$—C(=O)—NR$_a$R$_b$ group,
a —SO$_2$—NR$_a$R$_b$ group,
a —SO$_3$H group,
a —OH group,
a —O—SO$_2$—OR$_c$ group,
a —O—P(=O)—(OR$_c$)(OR$_d$) group,
a —O—CH$_2$—COOR$_c$ group,

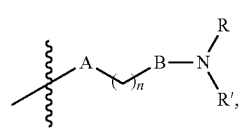

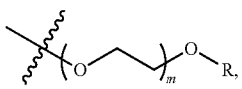

where:
A is a covalent bond, an oxygen atom, or NH,
B is a covalent bond or NH,
n is 1, 2, 3, 4 or 5,
m is 1, 2, or 3,
R, R', R$_a$, and R$_b$ independently represent a hydrogen atom, a ($C_1$-$C_5$)alkyl group, or a ($C_3$-$C_6$)cycloalkyl group,
R and R' can further form together with the nitrogen atom to which they are attached a saturated 5- or 6-membered heterocycle optionally containing a further heteroatom selected from N, O, and S, said heterocycle being optionally substituted by one or more R, $R_c$ and $R_d$ independently represent a hydrogen atom, $Li^+$, $Na^+$, $K^+$, $N^+(R_a)_4$ or a benzyl group, $R_5$ represents a hydrogen atom, a $(C_1-C_5)$alkyl group, or a $(C_3-C_6)$cycloalkyl group, $R_{10}$ is a hydrogen atom or a chlorine atom, and $R_{11}$ is a hydrogen atom or a $(C_1-C_4)$alkyl group;

provided that at least three of $R_5$, $R_7$, $R_8$, and $R_{10}$ are different from a hydrogen atom, or alternatively provided that one of $R_7$ and $R_8$ is a hydrogen atom and the other of $R_7$ and $R_8$ is a group selected from:

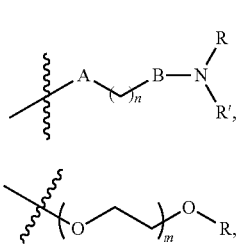

(IIa)

(IIIa)

a —$NR_a$—$SO_2$—$NR_aR_b$ group,
a —$NR_a$—$SO_2$—$R_a$ group,
a —$NR_a$—C(=O)—$R_a$ group, and a —$NR_a$—C(=O)—$NR_aR_b$ group, or alternatively provided that one of $R_0$, $R_1$, $R_2$, $R_3$ and $R_4$ is a group selected from:

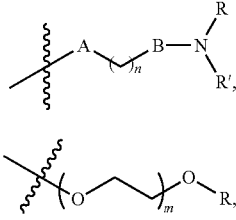

(IIa)

(IIIa)

a —$NR_a$—$SO_2$—$NR_aR_b$ group,
a —$NR_a$—$SO_2$—$R_a$ group,
a —$NR_a$—C(=O)—$R_a$ group, and
a —$NR_a$—C(=O)—$NR_aR_b$ group.

2. A compound of formula (I) or a pharmaceutically acceptable salt thereof:

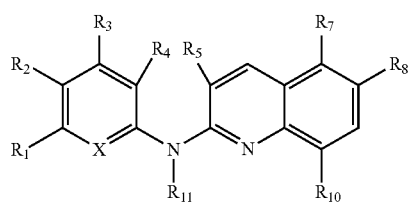

(I)

wherein:

X is $CR_0$ or N, i.e. forms together with the ring to which it belongs respectively a benzene or a pyridine group, $R_1$, $R_2$, $R_3$, $R_7$ and $R_8$ independently represent:
a hydrogen atom,
a halogen atom, or
a group selected from:
    a $(C_1-C_5)$alkyl group,
    a $(C_3-C_6)$cycloalkyl group,
    a $(C_1-C_5)$fluoroalkyl group,
    a $(C_1-C_5)$alkoxy group,
    a $(C_1-C_5)$fluoroalkoxy group,
    a —CN group,
    a —$COOR_a$ group,
    a —$NO_2$ group,
    a —$NR_aR_b$ group,
    a —$NR_a$—$SO_2$—$NR_aR_b$ group,
    a —$NR_a$—$SO_2$—$R_a$ group,
    a —$NR_a$—C(=O)—$R_a$ group,
    a —$NR_a$—C(=O)—$NR_aR_b$ group,
    a —$SO_2$—$NR_aR_b$ group,
    a —$SO_3H$ group,
    a —OH group,
    a —O—$SO_2$—$OR_c$ group,
    a —O—P(=O)—$(OR_c)(OR_d)$ group,
    a —O—$CH_2$—$COOR_c$ group,

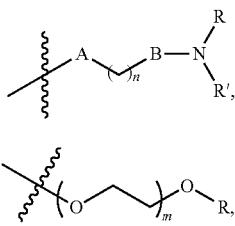

(IIa)

(IIIa)

where:
A is a covalent bond, an oxygen atom, or NH,
B is a covalent bond or NH,
n is 1, 2, 3, 4, or 5,
m is 1, 2, or 3,
R, R', $R_a$, and $R_b$ independently represent a hydrogen atom, a $(C_1-C_5)$alkyl group, or a $(C_3-C_6)$cycloalkyl group,
R and R' can further form together with the nitrogen atom to which they are attached a saturated 5- or 6-membered heterocycle optionally containing a further heteroatom selected from N, O, and S, said heterocycle being optionally substituted by one or more R,
$R_c$ and $R_d$ independently represent a hydrogen atom, $Li^+$, $Na^+$, $K^+$, $N^+(R_a)_4$ or a benzyl group,
$R_0$ represents a hydrogen atom or a $(C_1-C_5)$alkyl group,
$R_4$ represents a hydrogen atom or a $(C_1-C_5)$alkyl group when X is $CR_0$,
$R_4$ is has the same definition as $R_1$, $R_2$, $R_3$, $R_7$, and $R_8$ above when X is N,
$R_5$ represents a hydrogen atom, a $(C_1-C_5)$alkyl group, or a $(C_3-C_6)$cycloalkyl group,
$R_{10}$ is a hydrogen atom or a chlorine atom, and
$R_{11}$ is a hydrogen atom or a $(C_1-C_4)$alkyl group;
provided that at least three of $R_5$, $R_7$, $R_8$, and $R_{10}$ are different from a hydrogen atom, or alternatively provided that one of $R_7$ and $R_8$ is a hydrogen atom and the other of $R_7$ and $R_8$ is a group selected from:

![structure (IIa)]

![structure (IIIa)]

a —NR$_a$—SO$_2$—NR$_a$R$_b$ group,
a —NR$_a$—SO$_2$—R$_a$ group,
a —NR$_a$—C(=O)—R$_a$ group, and
a —NR$_a$—C(=O)—NR$_a$R$_b$ group, or alternatively provided that one of R$_1$, R$_2$, R$_3$, and R$_4$ is a group selected from:

![structure (IIa)]

![structure (IIIa)]

a —NR$_a$—SO$_2$—NR$_a$R$_b$ group,
a —NR$_a$—SO$_2$—R$_a$ group,
a —NR$_a$—C(=O)—R$_a$ group, and
a —NR$_a$—C(=O)—NR$_a$R$_b$ group;

wherein:
when R$_2$ is —OH, then neither R$_1$ nor R$_3$ is a

![structure]

radical, when R$_8$ is a methoxy group then neither R$_1$ nor R$_3$ is a

![structure]

radical, when R$_8$ is a —NH—C(=O)—CH$_3$ group then R$_2$ is not a —N(CH$_3$)$_2$ group, and the following compounds are excluded from the scope of compounds of formula ![four excluded compound structures] •HCl and 3. The compound of formula (I) or a pharmaceutically acceptable salt thereof according to claim 2, wherein:
when X is N, R$_4$ is a hydrogen atom, a fluorine atom, a NO$_2$ group, a NH$_2$ group, a methyl group, a methoxy group, a trifluoromethoxy group,
a —N—SO$_2$—N(CH$_3$)$_2$ group, a —N—SO$_2$—CH$_3$ group, a —N—C(=O)—CH$_3$ group, or
a —N—C(=O)—NR$_a$R$_b$ group,
R$_1$ and R$_3$ independently represent a hydrogen atom, a methyl group, a trifluoromethyl group, a chlorine atom, a methoxy group, a trifluoromethoxy group, or a group selected from:

![two structures] and

X$_1$ is O, N(CH$_3$), or CH$_2$,
m is 1 or 2,
R$_2$ is a hydrogen atom, a fluorine atom, a methyl group, a trifluoromethyl group, a NH$_2$ group, a methoxy group, a trifluoromethoxy group, a —O—CH$_2$—CH$_2$—OH group,
a —N—SO$_2$—N(CH$_3$)$_2$ group, a —N—SO$_2$—CH$_3$ group, a —N—C(=O)—CH$_3$ group, or a —N—C(=O)—NR$_a$R$_b$ group, $R_5$ represents a hydrogen atom or a methyl group, $R_7$ is a hydrogen atom, a $NH_2$ group, or when $R_8$ is a hydrogen atom, $R_7$ can further be a group selected from:

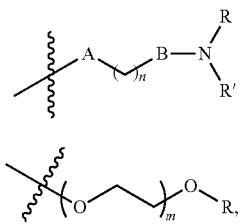

(IIa)

(IIIa)

a —N—SO$_2$—N(CH$_3$)$_2$ group, a —N—SO$_2$—CH$_3$ group, a —N—C(=O)—CH$_3$ group, and a —N—C(=O)—N($R_a$)($R_b$) group, n is 1, 2 or 3, $R_8$ is a hydrogen atom, a $NH_2$ group, or when $R_7$ is a hydrogen atom, $R_8$ can further be a group selected from:

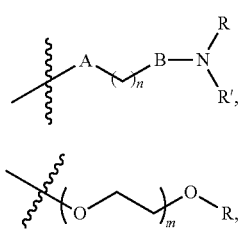

(IIa)

(IIIa)

$R_{10}$ is a hydrogen atom or a chlorine atom, and $R_{11}$ is a hydrogen atom or a (C$_1$-C$_4$)alkyl group, provided that at least three of $R_5$, $R_7$, $R_8$ and $R_{10}$ are different from a hydrogen atom, or alternatively provided that one of $R_7$ and $R_8$ is a hydrogen atom and the other of $R_7$ and $R_8$ is a group selected from:

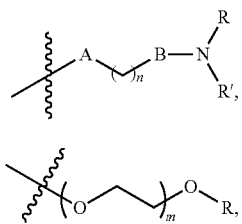

(IIa)

(IIIa)

$R_7$ being further able to be a —N—SO$_2$—N(CH$_3$)$_2$ group, a —N—SO$_2$—CH$_3$ group, a —N—C(=O)—CH$_3$ group, or a —N—C(=O)—NR$_a$R$_b$ group when $R_8$ is a hydrogen atom, or alternatively provided that $R_1$ or $R_3$ is a group selected from:

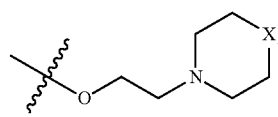 and

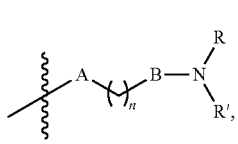

or alternatively provided that $R_2$, or $R_4$ when X is N, is a group selected from a —N—SO$_2$—N(CH$_3$)$_2$ group, a —N—SO$_2$—CH$_3$ group, a —N—C(=O)—CH$_3$ group, and a —N—C(=O)—NR$_a$R$_b$ group, and provided that the following compound is excluded:

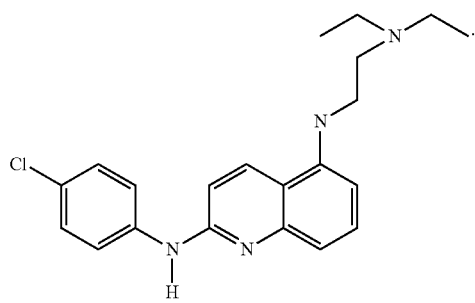 [SMILES: CCN(CC)CCNc1cccc2nc(Nc3ccc(Cl)cc3)ccc12]

4. The compound of formula (I) according to claim 2, wherein the compound is a compound of formula (A1) or a pharmaceutically acceptable salt thereof:

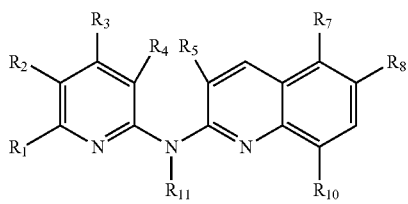

(A1)

wherein:

$R_1$ and $R_3$ independently represents a hydrogen atom, a methyl group, or a trifluoromethyl group, $R_2$ is a hydrogen atom, a fluorine atom, a methyl group, a trifluoromethyl group, a $NH_2$ group, a N—SO$_2$—N(CH$_3$)$_2$ group, a —N—SO$_2$—CH$_3$ group, a —N—C(=O)—CH$_3$ group, or a —N—C(=O)—NR$_a$R$_b$ group, $R_4$ is a hydrogen atom, a $NO_2$ group, a $NH_2$ group, a fluorine atom, a methyl group, a —N—SO$_2$—N(CH$_3$)$_2$ group, a —N—SO$_2$—CH$_3$ group, a —N—C(=O)—CH$_3$ group or a —N—C(=O)—NR$_a$R$_b$ group, $R_5$ is a hydrogen atom or a methyl group, $R_7$ is a hydrogen atom, a $NH_2$ group, or when $R_8$ is a hydrogen atom, $R_7$ is a group selected from:

(IIa)

-continued

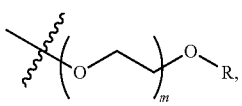 (IIIa)

a —N—SO$_2$—N(CH$_3$)$_2$ group, a —N—SO$_2$—CH$_3$ group, a —N—C(=O)—CH$_3$ group, and a —N—C(=O)—NR$_a$R$_b$ group, n is 1, 2, or 3, m is 1 or 2, R$_8$ is a hydrogen atom, a NH$_2$ group, or when R$_7$ is a hydrogen atom, R$_8$ can further be a group selected from:

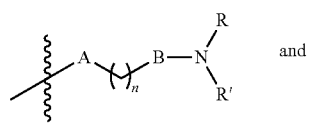 (IIa)

and

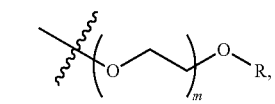 (IIIa)

R$_{10}$ is a hydrogen atom or a chlorine atom, provided that at least three of R$_5$, R$_7$, R$_8$, and R$_{10}$ are different from a hydrogen atom, or alternatively provided that one of R7 and R8 is a hydrogen atom and the other of R$_7$ and R$_8$ is a group selected from:

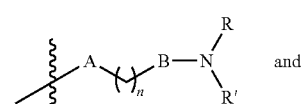 (IIa)

and

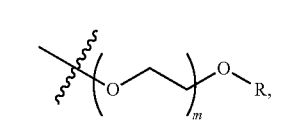 (IIIa)

R$_7$ being further able to be a —N—SO$_2$—N(CH$_3$)$_2$ group, a —N—SO$_2$—CH$_3$ group, a —N—C(=O)—CH$_3$ group, or a —N—C(=O)—NR$_a$R$_b$ group when R$_8$ is a hydrogen atom, or alternatively provided that R$_2$ or R$_4$ is a group selected from a —N—SO$_2$—N(CH$_3$)$_2$ group, a —N—SO$_2$—CH$_3$ group, a —N—C(=O)—CH$_3$ group, and a —N—C(=O)—NR$_a$R$_b$ group.

5. The compound of formula (I) according to claim 2, wherein the compound is a compound of formula (B1) or a pharmaceutically acceptable salt thereof:

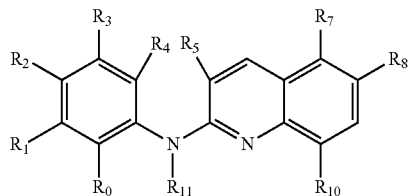 (B1)

wherein:

R$_0$ and R$_4$ are independently a hydrogen atom, or a methyl group,

R$_1$ and R$_3$ independently represent a hydrogen atom, a chlorine atom, a methoxy group, a trifluoromethoxy group, or a group selected from:

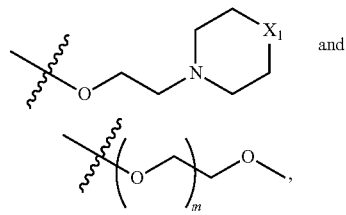

and

X$_1$ is O, N(CH$_3$), or CH$_2$, m is 1 or 2,

R$_2$ is a hydrogen atom, a methoxy group, a trifluoromethoxy group, or a —O—CH$_2$—CH$_2$—OH group, R$_5$ is a hydrogen atom or a methyl group, R$_7$ is a hydrogen atom, a NH$_2$ group, or when R$_8$ is a hydrogen atom, R$_7$ is a group selected from:

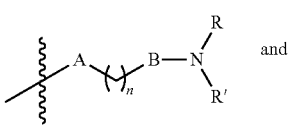 (IIa)

(IIIa)

a —N—SO$_2$—N(CH$_3$)$_2$ group, a —N—SO$_2$—CH$_3$ group, a —N—C(=O)—CH$_3$ group, and a —N—C(=O)—NR$_a$R$_b$ group, n is 1, 2, or 3, R$_8$ is a hydrogen atom, a NH$_2$ group, or when R$_7$ is a hydrogen atom, R$_8$ can further be a group selected from:

(IIa)

-continued

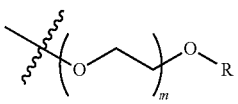
(IIIa)

$R_{10}$ is a hydrogen atom or a chlorine atom,
provided that at least three of $R_5$, $R_7$, $R_8$ and $R_{10}$ are different from a hydrogen atom, or alternatively
provided that one of $R_7$ and $R_8$ is a hydrogen atom and the other of $R_7$ and $R_8$ is a group selected from:

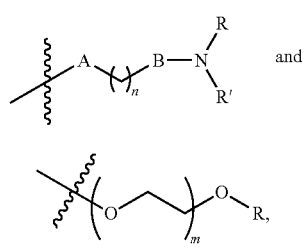
(IIa)

and

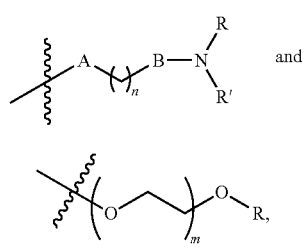
(IIIa)

$R_7$ being further able to be a —N—SO$_2$—N(CH$_3$)$_2$ group, a —N—SO$_2$—CH$_3$ group, a —N—C(=O)—CH$_3$ group, or a —N—C(=O)—NR$_a$R$_b$ group when $R_8$ is a hydrogen atom, or alternatively
provided that $R_1$ or $R_3$ is a group selected from:

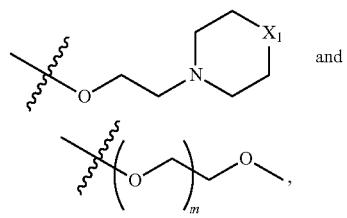

and or alternatively
provided that $R_2$ is a group selected from a —N—SO$_2$—N(CH$_3$)$_2$ group, a —N—SO$_2$—CH$_3$ group, a —N—C(=O)—CH$_3$ group, and a —N—C(=O)—NR$_a$R$_b$ group, and
provided that the following compound is excluded:

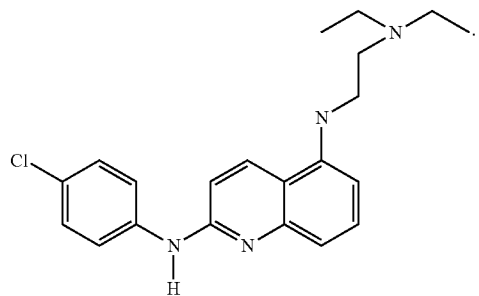 [SMILES: CCN(CC)CCNc1cccc2nc(Nc3ccc(Cl)cc3)ccc12]

6. The compound of formula (I) or a pharmaceutically acceptable salt thereof according to claim 2, wherein:
X is N,
$R_1$, $R_2$, $R_8$, and $R_{11}$ are each a hydrogen atom,
$R_3$ is a methyl group or a trifluoromethyl group, $R_4$ is a hydrogen atom or a NH$_2$ group,
$R_5$ is a hydrogen atom or a methyl group,
$R_7$ is a hydrogen atom, a NH$_2$ group, or when $R_8$ is a hydrogen atom, $R_7$ can further be a group selected from:

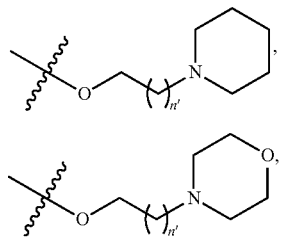

and a —N—SO$_2$—N(CH$_3$)$_2$ group,
n' is 0, 1, or 2 and
$R_{10}$ is a hydrogen atom or a chlorine atom,
provided that at least three of $R_5$, $R_7$, $R_8$, and $R_{10}$ are different from a hydrogen atom, or alternatively
provided that $R_7$ is a group selected from:

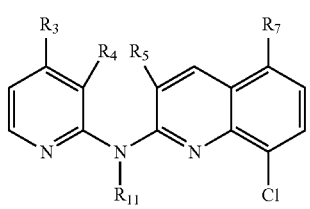

and a —N—SO$_2$—N(CH$_3$)$_2$ group.

7. The compound of formula (I) according to claim 2, wherein the compound is a compound of formula (A1') or a pharmaceutically acceptable salt thereof:

(A1')

wherein:
$R_3$ is a hydrogen atom, a methyl group, or a trifluoromethyl group,
$R_4$ is a hydrogen atom, a NO$_2$ group, a NH$_2$ group, a fluorine atom, a methyl group, a —N—SO$_2$—N(CH$_3$)$_2$ group, —N—SO$_2$—CH$_3$ group, a —N—C(=O)—CH$_3$ group, or a —N—C(=O)—NR$_a$R$_b$ group,
$R_5$ is a hydrogen atom or a methyl group,
$R_7$ is a hydrogen atom, a NH$_2$ group, or a group selected from:

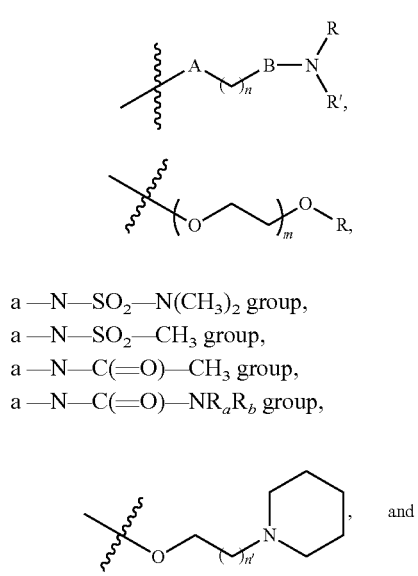

a —N—SO$_2$—N(CH$_3$)$_2$ group,
a —N—SO$_2$—CH$_3$ group,
a —N—C(=O)—CH$_3$ group,
a —N—C(=O)—NR$_a$R$_b$ group,

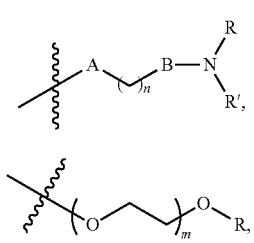

n is 1, 2 or 3,
n' is 0, 1 or 2,
m is 1 or 2,
provided that R$_5$ and R$_7$ are not hydrogen atom, or alternatively
provided that R$_5$ is a hydrogen atom and R$_7$ is selected from (IIa)

(IIIa)

a —N—SO$_2$—N(CH$_3$)$_2$ group,
a —N—SO$_2$—CH$_3$ group,
a —N—C(=O)—CH$_3$ group, and
a —N—C(=O)—NR$_a$R$_b$ group, or alternatively
provided that R$_7$ is a hydrogen atom and R$_4$ is selected from a —N—SO$_2$—N(CH$_3$)$_2$ group, —N—SO$_2$—CH$_3$ group, a —N—C(=O)—CH$_3$ group, and a —N—C(=O)—NR$_a$R$_b$ group.

8. The compound of formula (I) according to claim 2 or a pharmaceutically acceptable salt thereof, wherein:
X is CR$_0$,
R$_0$, R$_1$, R$_4$, R$_8$ and R$_{11}$ are independently a hydrogen atom,
R$_2$ is a methoxy group, a trifluoromethoxy group, or a —O—CH$_2$—CH$_2$—OH group,
R$_3$ is a hydrogen atom, a chlorine atom, or a group selected from:

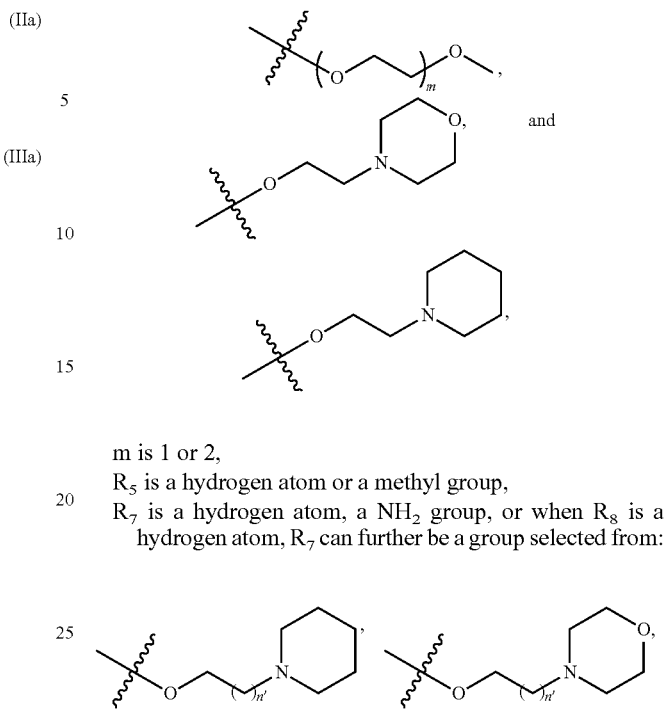

m is 1 or 2,
R$_5$ is a hydrogen atom or a methyl group,
R$_7$ is a hydrogen atom, a NH$_2$ group, or when R$_8$ is a hydrogen atom, R$_7$ can further be a group selected from:

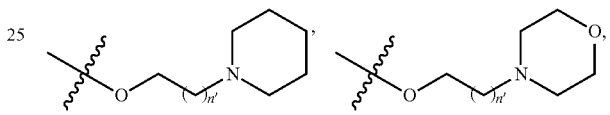

and a —NH—SO$_2$—N(CH$_3$)$_2$ group,
n' is 0, 1, or 2, and
R$_{10}$ is a hydrogen atom or a chlorine atom,
provided that at least three of R$_5$, R$_7$, R$_8$, and R$_{10}$ are different from a hydrogen atom, or alternatively
provided that R$_7$ is a group selected from:

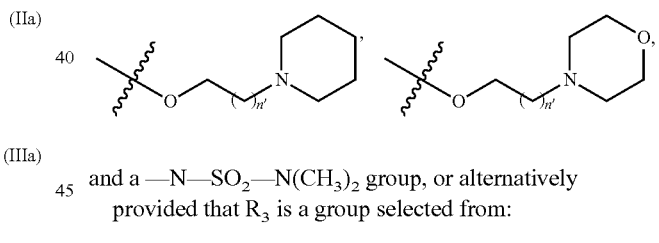

and a —N—SO$_2$—N(CH$_3$)$_2$ group, or alternatively
provided that R$_3$ is a group selected from:

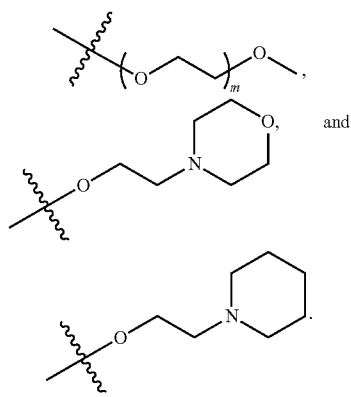

9. The compound of formula (I) according to claim 2, wherein the compound is a compound of formula (B1') or a pharmaceutically acceptable salt thereof:

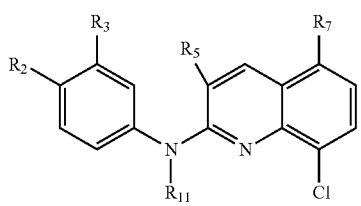
(B1′)

wherein:
R₂ is a hydrogen atom, a methoxy group, a trifluoromethoxy group, or a —O—CH₂—CH₂—OH group,
R₃ is a hydrogen atom, a chlorine atom, a methoxy group, a trifluoromethoxy group, a —O—CH₂—CH₂—O—CH₂—CH₂—O—CH₃ group, or a group selected from:

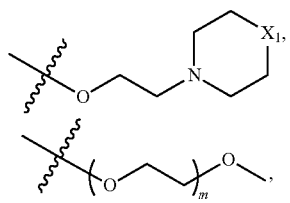

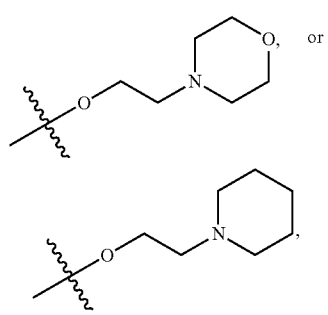

X₁ is O, N(CH₃) or CH₂,
m is 1 or 2,
R₅ is a hydrogen atom or a methyl group,
R₇ is a hydrogen atom, a NH₂ group, or when R₈ is a hydrogen atom, R₇ is a group selected from:

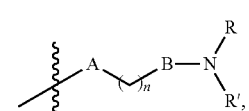
(IIa)

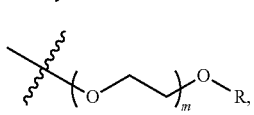
(IIIa)

a —N—SO₂—N(CH₃)₂ group,
a —N—SO₂—CH₃ group,
a —N—C(=O)—CH₃ group,
a —N—C(=O)—NRₐR_b group,
a —NH—SO₂—N(CH₃)₂ group,

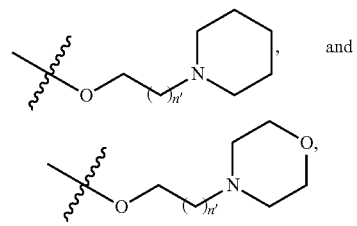
and n′ is 0, 1, or 2,
n is 1, 2 or 3,
provided that R₅ and R₇ are not a hydrogen atom, or alternatively
provided that R₅ is a hydrogen atom and R₇ is a group selected from:

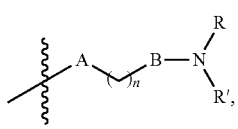
(IIa)

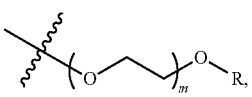
(IIIa)

a —N—SO₂—N(CH₃)₂ group,
a —N—SO₂—CH₃ group,
a —N—C(=O)—CH₃ group, and
a —N—C(=O)—NRₐR_b group, or alternatively
provided that R₇ is a hydrogen atom and R₃ is a group selected from:

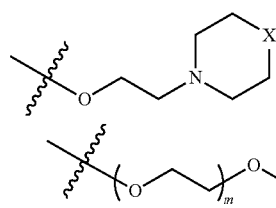
and

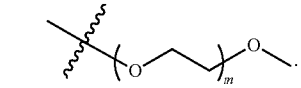

10. A compound selected from:
(1) 8-chloro-5-(2-morpholinoethoxy)-N-(4-(trifluoromethyl)pyridin-2-yl)quinolin-2-amine,
(2) N2-(8-chloro-5-(2-morpholinoethoxyl)quinolin-2-yl)-4-methylpyridine-2,3-diamine,
(3) 8-chloro-5-(2-(piperidin-1-yl)ethoxy)-N-(4-(trifluoromethyl)pyridin-2-yl)quinolin-2-amine,
(4) 8-chloro-3-methyl-5-(2-(piperidin-1-yl)ethoxy)-N-(4-(trifluoromethyl)pyridin-2-yl)quinolin-2-amine,
(5) N2-(8-chloro-3-methyl-5-(2-(piperidin-1-yl)ethoxy)quinolin-2-yl)-4-methylpyridine-2,3-diamine,
(6) N,N-dimethyl-N′-[2-[(4-trifluoromethylpyridin-2-yl)amino]-8-chloro-5-quinolinyl]sulfamide,
(7) N,N-dimethyl-N′-[2-[(4-trifluoromethylpyridin-2-yl)amino]-3-methyl-5-quinolinyl]sulfamide,
(8) 8-chloro-3-methyl-N2-(4-(trifluoromethyl)pyridin-2-yl)quinoline-2,5-diamine,
(9) N,N-dimethyl-N′-[2-[(4-trifluoromethyl-pyridin-2-yl)amino]-8-chloro-3-methyl-5-quinolinyl]sulfamide,
(10) N′-[2-[(3-amino-4-methylpyridin-2-yl)amino]-8-chloro-5-quinolinyl]N,N-dimethylsulfamide,

(11) N'-[2-[(3-amino-4-methylpyridin-2-yl)amino]-8-chloro-3-methyl-5-quinolinyl]-N,N-dimethylsulfamide,
(12) N2-(3-amino-4-methylpyridin-2-yl)-8-chloro-3-methylquinoline-2,5-diamine,
(13) N'-[2-[(-3-amino-4-methylpyridin-2-yl)amino]-3-methyl-5-quinolinyl]-N,N-dimethylsulfamide,
(14) 8-chloro-5-(2-(piperidin-1-yl)ethoxy)-N-(4-(trifluoromethoxy)phenyl)quinolin-2-amine,
(15) 8-chloro-3-methyl-5-(2-(piperidin-1-yl)ethoxy)-N-(4-(trifluoromethoxy)phenyl)quinolin-2-amine,
(16) 8-chloro-N-(3-chloro-4-(trifluoromethoxy)phenyl)-5-(2-(piperidin-1-yl)ethoxy)quinolin-2-amine,
(17) 8-chloro-N-(3-chloro-4-methoxyphenyl)-5-(2-morpholinoethoxyl)quinolin-2-amine,
(18) 8-chloro-N2-(3-chloro-4-(trifluoromethoxy)phenyl)-3-methylquinoline-2,5-diamine,
(19) N'-[2-[(3-chloro-4-(trifluoromethoxy)phenyl)amino]-3-methyl-5-quinolinyl]-N,N-dimethylsulfamide,
(20) N'-[2-[(3-chloro-4-(trifluoromethoxy)phenyl)amino]-8-chloro-5-quinolinyl]-N,N-dimethylsulfamide,
(21) N'-[2-[(3-chloro-4-(trifluoromethoxy)phenyl)amino]-8-chloro-3-methyl-5-quinolinyl]-N,N-dimethylsulfamide,
(22) 2-(4-((8-chloroquinolin-2-yl)amino)phenoxy)ethanol,
(23) 8-chloro-N-(4-methoxy-3-(2-morpholinoethoxyl)phenyl)quinolin-2-amine,
(24) 8-chloro-N-(4-methoxy-3-(2-(2-methoxyethoxyl)ethoxy)phenyl)quinolin-2-amine,
(25) 8-chloro-N-(4-methoxy-3-(2-(piperidin-1-yl)ethoxy)phenyl)quinolin-2-amine,
(26) N-[3-methyl-2-[(4-trifluoromethylpyridin-2-yl)amino]-5-quinolinyl]-methanesulfonamide,
(27) N-[2-[(3-chloro-4-(trifluoromethoxy)phenyl)amino]-3-methyl-5-quinolinyl]-methanesulfonamide; and and their pharmaceutically acceptable salts selected from hydrobromide, tartrate, citrate, trifluoroacetate, ascorbate, hydrochloride, tartrate, triflate, maleate, mesylate, formate, acetate, and fumarate salts.

11. A pharmaceutical composition comprising at least one compound of formula (I) or a pharmaceutically acceptable salt thereof as defined in claim 2.

12. A medicament, comprising a compound of formula (I) or a pharmaceutically acceptable salt thereof according to claim 2.

13. A method of treating a subject with a disease resulting from at least one splicing anomaly, comprising administering to the subject an effective amount of a compound of formula (I) or a pharmaceutically acceptable salt thereof according to claim 2.

14. A method of inhibiting replication of HIV-1 in a patient infected with HIV-1, comprising administrating to the patient an effective quantity of a compound of formula (I) or a pharmaceutically acceptable salt thereof according to claim 2 to inhibit replication of HIV-1.

* * * * *